United States Patent [19]

Chakravarty et al.

[11] Patent Number: 5,236,928
[45] Date of Patent: Aug. 17, 1993

[54] IMIDAZOLE DERIVATIVES BEARING ACIDIC FUNCTIONAL GROUPS AT THE 5-POSITION, THEIR COMPOSITIONS AND METHODS OF USE AS ANGIOTENSIN II ANTAGONISTS

[75] Inventors: Prasun K. Chakravarty, Edison; William J. Greenlee, Teaneck; Arthur A. Patchett, Westfield, all of N.J.

[73] Assignee: Merck & Co., Inc., Rahway, N.J.

[21] Appl. No.: 891,668

[22] Filed: May 29, 1992

Related U.S. Application Data

[63] Continuation of Ser. No. 671,597, Mar. 19, 1991, abandoned.

[51] Int. Cl.[5] .......... A61K 31/505; A61K 31/415; A61K 31/42; C07D 403/12; C07D 403/14
[52] U.S. Cl. .................. 514/275; 514/380; 514/381; 514/235.8; 514/398; 514/400; 544/122; 544/137; 544/139; 544/297; 548/323.5; 548/324.1; 548/326.5; 548/333.5; 548/334.5; 548/338.5; 548/340.1; 548/253; 548/246
[58] Field of Search .......... 548/335, 336, 339, 343, 548/346, 253, 246, 323.5, 324.1, 326.5, 333.5, 334.5, 338.5, 340.1, 337; 514/396, 398, 399, 400, 380, 381, 235.8, 275; 544/122, 139, 137, 297

[56] References Cited

FOREIGN PATENT DOCUMENTS

| 58696/90 | 1/1991 | Australia . |
|---|---|---|
| 0411766 | 2/1991 | Australia . |
| 0253310 | 1/1988 | European Pat. Off. . |
| 409332 | 1/1988 | European Pat. Off. . |
| 0260613 | 3/1988 | European Pat. Off. . |
| 0323841 | 7/1989 | European Pat. Off. . |
| 0324377 | 7/1989 | European Pat. Off. . |
| 0400974 | 5/1990 | European Pat. Off. . |
| 0392317 | 10/1990 | European Pat. Off. . |
| 0399731 | 11/1990 | European Pat. Off. . |
| 0399732 | 11/1990 | European Pat. Off. . |
| 0403158 | 12/1990 | European Pat. Off. . |
| 0403159 | 12/1990 | European Pat. Off. . |
| 0412594 | 2/1991 | European Pat. Off. . |
| 0415886 | 3/1991 | European Pat. Off. . |
| 0419048 | 3/1991 | European Pat. Off. . |
| 0429257 | 5/1991 | European Pat. Off. . |
| 8911855 | 5/1989 | United Kingdom . |
| 9005843 | 3/1990 | United Kingdom . |

OTHER PUBLICATIONS

Burger, A., Medicinal Chemistry, 2nd Ed., 1960, pp. 565-571, 578-581, 600-601.

*Primary Examiner*—Floyd D. Higel
*Assistant Examiner*—Lenora A. Miltenberger
*Attorney, Agent, or Firm*—Valerie J. Camara; William H. Nicholson; Joseph F. DiPrima

[57] ABSTRACT

There are disclosed substituted imidazole derivatives of Formula I bearing acidic functional groups which are useful as angiotensin II antagonists.

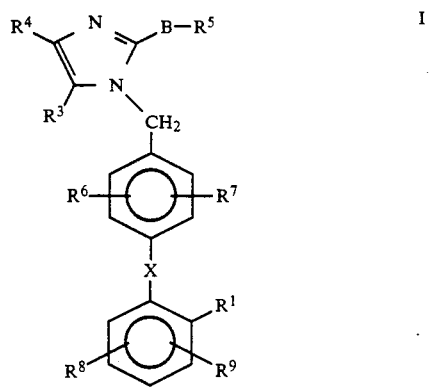

8 Claims, No Drawings

IMIDAZOLE DERIVATIVES BEARING ACIDIC FUNCTIONAL GROUPS AT THE 5-POSITION, THEIR COMPOSITIONS AND METHODS OF USE AS ANGIOTENSIN II ANTAGONISTS

This is a continuation of application Ser. No. 07/671,597 filed on Mar. 19, 1991, now abandoned.

BACKGROUND OF THE INVENTION

The Renin-angiotensin system (RAS) plays a central role in the regulation of normal blood pressure and seems to be critically involved in hypertension development and maintenance as well as congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the reninangiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; and 4,582,847 in European Patent Applications 028,834; 245,637; 253,310; and 291,969; and in articles by A. T. Chiu, et al. [*Eur. J. Pharm. Exp. Therap*, 157, 13–21 (1988)] and by P. C. Wong, et al. [*J. Pharm. Exp. Therap*, 247, 1–7(1988)]. All of the U.S. patents, European Patent Applications 028,834, 253,310, 324,377, 403,158 and 403,159 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]pyridine-6-carboxylic acid and analogs thereof as antihypertensive agents.

None of the compounds disclosed in this application have been identified in any U.S. Patent, European Applications or articles. The substituted imidazoles, have been disclosed in European Patent Applications 253,310, 324,377, 403,158 and 403,159 focusing on the design of Angiotensin II Antagonists.

BRIEF DESCRIPTION OF THE INVENTION

This invention is directed to novel substituted imidazole compounds of formula (I) which bear potentially acidic functional groups. Specifically, the compounds of this invention contain an imidazole moiety which is substituted at the 5 position with novel acidic groups and at the 1 position with substituted benzyl groups which bear potentially novel acid equivalent functional groups.

The compounds of formula (I) are angiotensin II antagonists and are useful in the treatment of hypertension and congestive heart failure. Additionally, pharmaceutically acceptable compositions of these novel compounds, as the sole therapeutically active ingredient and in combination with diuretics and other antihypertensive agents, including beta-blockers, angiotensin converting enzyme inhibitors, calcium channel blockers or a combination thereof are disclosed. Further, methods of treating hypertension, congestive heart failure and elevated intraocular pressure are also described.

DETAILED DESCRIPTION OF THE INVENTION

This invention relates to compounds having the formula:

TABLE 2

| Test Compound | BALB 3T3/H-ras Inhibition Activity IC$_{50}$ (μg/ml) |
|---|---|
| UCA1064-B | 3.5 |

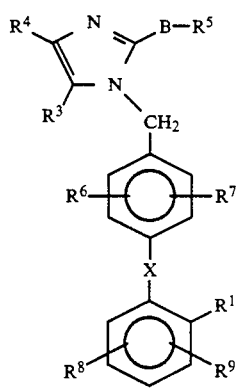

wherein:
$R^1$ is
(a) —$CO_2R^{10}$,
(b) —$PO(OR^{14})_2$,
(c) —$NHSO_2R^{12}$,
(d) —$SO_2NHR^{12}$, (e) 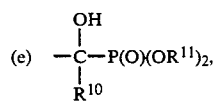

(f) 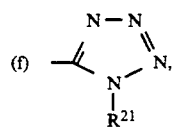

(g) 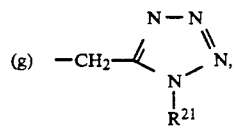

(h) 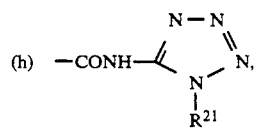

(i) —$CONHNHSO_2CF_3$, (j) 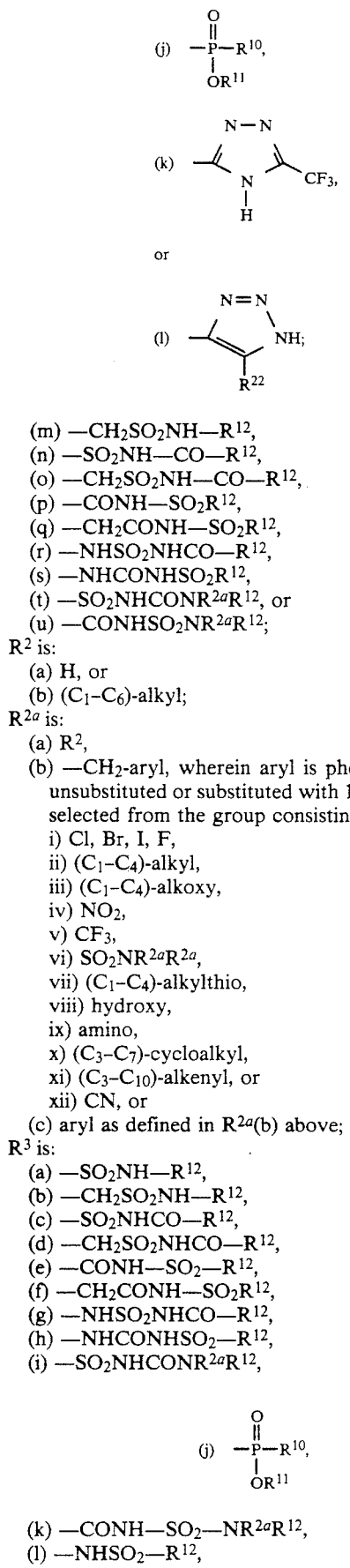

(m) —CH$_2$SO$_2$NH—R$^{12}$,
(n) —SO$_2$NH—CO—R$^{12}$,
(o) —CH$_2$SO$_2$NH—CO—R$^{12}$,
(p) —CONH—SO$_2$R$^{12}$,
(q) —CH$_2$CONH—SO$_2$R$^{12}$,
(r) —NHSO$_2$NHCO—R$^{12}$,
(s) —NHCONHSO$_2$R$^{12}$,
(t) —SO$_2$NHCONR$^{2a}$R$^{12}$, or
(u) —CONHSO$_2$NR$^{2a}$R$^{12}$;

R$^2$ is:
(a) H, or
(b) (C$_1$–C$_6$)-alkyl;

R$^{2a}$ is:
(a) R$^2$,
(b) —CH$_2$-aryl, wherein aryl is phenyl or naphthyl unsubstituted or substituted with 1 or 2 substituents selected from the group consisting of:
  i) Cl, Br, I, F,
  ii) (C$_1$–C$_4$)-alkyl,
  iii) (C$_1$–C$_4$)-alkoxy,
  iv) NO$_2$,
  v) CF$_3$,
  vi) SO$_2$NR$^{2a}$R$^{2a}$,
  vii) (C$_1$–C$_4$)-alkylthio,
  viii) hydroxy,
  ix) amino,
  x) (C$_3$–C$_7$)-cycloalkyl,
  xi) (C$_3$–C$_{10}$)-alkenyl, or
  xii) CN, or
(c) aryl as defined in R$^{2a}$(b) above;

R$^3$ is:
(a) —SO$_2$NH—R$^{12}$,
(b) —CH$_2$SO$_2$NH—R$^{12}$,
(c) —SO$_2$NHCO—R$^{12}$,
(d) —CH$_2$SO$_2$NHCO—R$^{12}$,
(e) —CONH—SO$_2$—R$^{12}$,
(f) —CH$_2$CONH—SO$_2$R$^{12}$,
(g) —NHSO$_2$NHCO—R$^{12}$,
(h) —NHCONHSO$_2$—R$^{12}$,
(i) —SO$_2$NHCONR$^{2a}$R$^{12}$, (j) 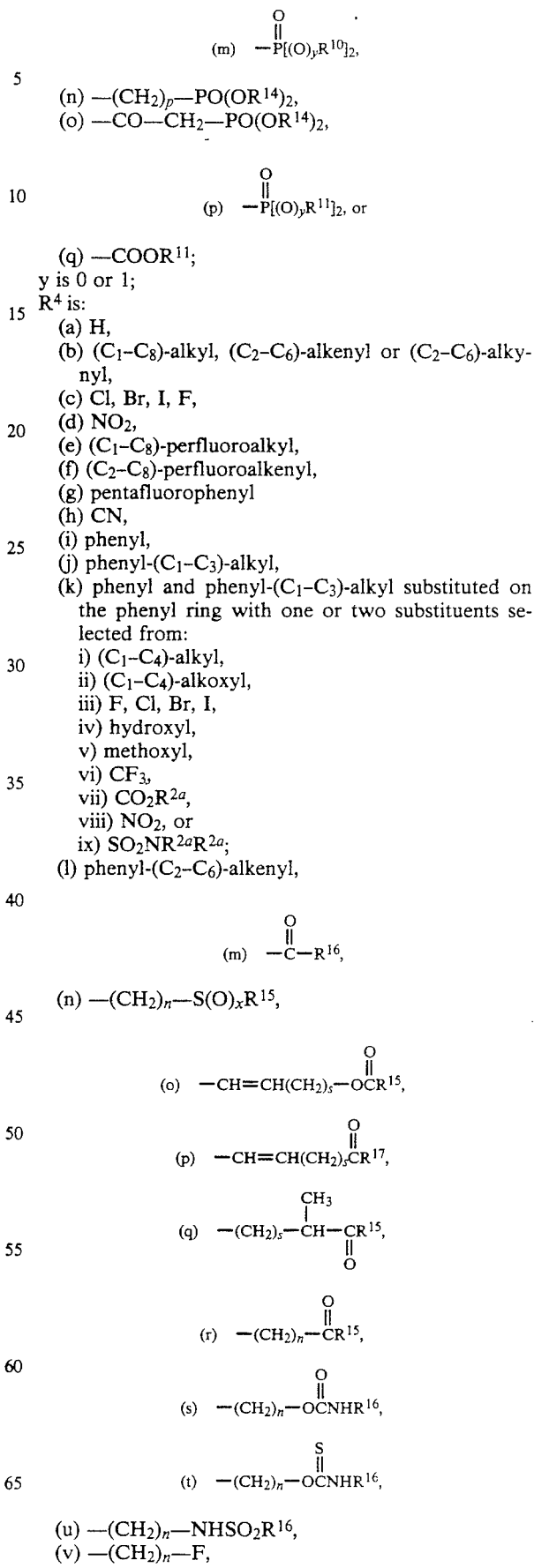

(k) —CONH—SO$_2$—NR$^{2a}$R$^{12}$,
(l) —NHSO$_2$—R$^{12}$, (n) —(CH$_2$)$_p$—PO(OR$^{14}$)$_2$,
(o) —CO—CH$_2$—PO(OR$^{14}$)$_2$, (q) —COOR$^{11}$;

y is 0 or 1;

R$^4$ is:
(a) H,
(b) (C$_1$–C$_8$)-alkyl, (C$_2$–C$_6$)-alkenyl or (C$_2$–C$_6$)-alkynyl,
(c) Cl, Br, I, F,
(d) NO$_2$,
(e) (C$_1$–C$_8$)-perfluoroalkyl,
(f) (C$_2$–C$_8$)-perfluoroalkenyl,
(g) pentafluorophenyl
(h) CN,
(i) phenyl,
(j) phenyl-(C$_1$–C$_3$)-alkyl,
(k) phenyl and phenyl-(C$_1$–C$_3$)-alkyl substituted on the phenyl ring with one or two substituents selected from:
  i) (C$_1$–C$_4$)-alkyl,
  ii) (C$_1$–C$_4$)-alkoxyl,
  iii) F, Cl, Br, I,
  iv) hydroxyl,
  v) methoxyl,
  vi) CF$_3$,
  vii) CO$_2$R$^{2a}$,
  viii) NO$_2$, or
  ix) SO$_2$NR$^{2a}$R$^{2a}$;
(l) phenyl-(C$_2$–C$_6$)-alkenyl, (u) —(CH$_2$)$_n$—NHSO$_2$R$^{16}$,
(v) —(CH$_2$)$_n$—F, (w) —$(CH_2)_m$-imidazol-1-yl, (x) —$(CH_2)_m$-1,2,3-triazolyl, unsubstituted or substituted with one or two groups selected from the group consisting of:
   i) $CO_2CH_3$,
   ii) $(C_1-C_4)$-alkyl, (y) 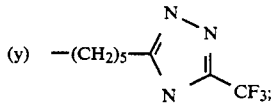

$R^5$ is:
(a) $(C_1-C_9)$-alkyl, $(C_2-C_6)$-alkenyl or $(C_2-C_6)$-alkynyl each of which is unsubstituted or substituted with a substituent selected from the group consisting of:
   i) aryl as defined in $R^{2a}$(b) above,
   ii) $(C_3-C_7)$-cycloalkyl,
   iii) Cl, Br, I, F,
   iv) $COOR^2$,
   vii) $N[\lambda(C_1-C_4)$-alkyl)$]_2$,
   viii) $NHSO_2R^2$,
   ix) $CF_3$,
   x) $COOR^2$, or
   xi) $SO_2NHR^{2a}$,
(b) aryl as defined in $R^{2a}$(b) above,
(c) an unsubstituted, monosubstituted or disubstituted heteroaromatic 5- or 6-membered cyclic moiety, which contains one or two members selected from the group consisting of N, O, S and wherein the substituents are members selected from the group consisting of:
   i) Cl, Br, I, F,
   ii) OH,
   iii) SH,
   iv) $NO_2$,
   v) $(C_1-C_4)$-alkyl,
   vi) $(C_2-C_4)$-alkenyl,
   vii) $(C_2-C_4)$-alkynyl,
   viii) $(C_1-C_4)$-alkoxy, or
   ix) $CF_3$, or
(d) perfluoro-$(C_1-C_4)$-perfluoroalkyl;

B is:
(a) a single bond,
(b) —$S(O)_x(CH_2)_s$—, or
(c) —O—;
x is 0 to 2;
s is 0 to 5;
p is 0 to 3;
n is 1 to 10;

$R^6$ is:
(a) H,
(b) Cl, Br, I, F,
(c) $(C_2-C_6)$-alkyl,
(d) $(C_2-C_6)$-alkoxy, or
(e) $(C_3-C_6)$-alkoxyalkyl;

$R^7$ is
(a) H,
(b) Cl, Br, I, F,
(c) $NO_2$,
(d) $(C_2-C_6)$-alkyl,
(e) $(C_2-C_6)$-acyloxy,
(f) $C_2-C_6$-cycloalkyl,
(g) $(C_2-C_6)$-alkoxy,
(h) —$NHSO_2R^{2a}$,
(i) hydroxy $(C_1-C_4)$-alkyl,
(j) $(C_1-C_4)$-alkyl-aryl, wherein aryl is defined in $R^{2a}$(b) above
(k) aryl-$(C_3-C_4)$-alkyl, wherein aryl is as defined in $R^{2a}$(b) above
(l) $(C_1-C_4)$-alkylthio,
(m) $(C_1-C_4)$-alkylsulfinyl,
(n) $(C_1-C_4)$-alkylsulfonyl,
(o) $NH_2$,
(p) $NH[(C_1-C_4)$-alkyl]
(q) $N[(C_1-C_4)$-alkyl$]_2$
(r) $(C_1-C_4)$-fluoroalkyl,
(s) —$SO_2$—$NHR^{10}$,
(t) aryl, as defined in $R^{2a}$(b) above
(u) furyl, or
(v) —$COOR^{11}$;

$R^8$ and $R^9$ are independently:
H, Cl, Br, I, F, —$NO_2$, —$NH_2$, $C_1-C_4$-alkylamino, di($C_1-C_4$ alkyl)amino, —$SO_2NHR^{10}$, $CF_3$, $C_1-C_6$-alkyl, $(C_1-C_6)$-alkoxy, $C_2-C_6$-alkenyl, $(C_2-C_6)$-alkynyl or when $R^8$ and $R^9$ are on adjacent carbon atoms, they are joined to form an aryl ring;

$R^{10}$ is H, $(C_1-C_5)$-alkyl, aryl or —$CH_2$-aryl wherein aryl is as defined in $R^{2a}$(b) above, $R^{11}$ is H or

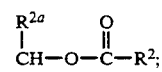

$R^{12}$ is
(a) aryl, as defined in $R^{2a}$(b) above
(b) heteroaryl, wherein heteroaryl is unsubstituted, monosubstituted or disubstituted five or six membered aromatic ring which contains from 1 to 3 heteroatoms selected from the group consisting of O, N or S and wherein the substituents are members selected from the group consisting of —OH, —SH, —$(C_1-C_4)$-alkyl, —$(C_1-C_4)$-alkoxy, —$CF_3$, Cl, Br, I, F, —$NO_2$, —$CO_2H$, $CO_2$—$(C_1-C_4)$-alkyl, —$NH_2$, —$NH[(C_1-C_4)$-alkyl], or —$N[(C_1-C_4)$-alkyl$]_2$,
(c) $(C_3-C_4)$-cycloalkyl,
(d) $(C_1-C_4)$-alkyl which is unsubstituted an substituted with a substituent that is a member selected from the group consisting of: aryl wherein aryl is as defined in $R^{2a}$(b) above, heteroaryl, —OH, —SH, $(C_1-C_4)$-alkyl, —O-$(C_1-C_4)$-alkyl, —$S(O)_x$-$(C_1-C_4)$-alkyl), —$CF_3$, Cl, Br, F, I, —$NO_2$, —$CO_2H$, —$CO_2$—$(C_1-C_4)$-alkyl, —$NH_2$, —$NH(C_1-C_4$-alkyl), —$NHCOR^{2a}$, —$N(C_1-C_4$-alkyl$)_2$, or

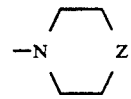

where Z is $NR^2$, O, $S(O)_x$, or
(e) $(C_1-C_4)$-perfluoroalkyl;

$R^{13}$ is:
(a) H,
(b) $(C_1-C_6)$-alkyl,
(c) aryl as defined in $R^{2a}$(b) above,
(d) aryl-$(C_1-C_6)$-alkyl-(C=O)—, wherein aryl is as defined in $R^{2a}$(b) above,
(e) $(C_1-C_6)$-alkyl-(C=O)—,
(f) $(C_3-C_6)$-cycloalkyl, or
(g) allyl; and $R^{14}$ is:
 (a) H,
 (b) $(C_1-C_8)$-alkyl,
 (c) phenyl, or
 (d) benzyl;

$R^{15}$ is:
 (a) H,
 (b) $(C_1-C_6)$-alkyl,
 (c) $(C_3-C_6)$-cycloalkyl,
 (d) $-(CH_2)_p$-phenyl,
 (e) $-OR^{17}$,
 (f) morpholin-4-yl, or
 (g) $-NR^{18}R^{19}$;

$R^{16}$ is:
 (a) $(C_1-C_8)$-alkyl,
 (b) $(C_1-C_8)$-perfluoroalkyl,
 (c) 1-adamantyl,
 (d) 1-naphthyl,
 (e) (1-naphthyl)ethyl, or
 (f) $-(CH_2)_p$-phenyl;

$R^{17}$ is:
 (a) H,
 (b) $(C_1-C_6)$-alkyl,
 (c) $(C_3-C_6)$-cycloalkyl,
 (d) phenyl, or
 (e) benzyl;

$R^{18}$ and $R^{19}$ are independently:
 (a) H,
 (b) $(C_1-C_4)$-alkyl,
 (c) phenyl,
 (d) benzyl, or
 (e) α-methylbenzyl;

$R^{20}$ is:
 (a) H,
 (b) $(C_1-C_6)$-alkyl,
 (c) $(C_3-C_6)$-cycloalkyl, or
 (d) $-CH_2$-aryl wherein aryl is as defined in $R^{2a}$(b) above;

$R^{21}$ is:
 (a) H,
 (b) $(C_1-C_6)$-alkyl,
 (c) $(C_2-C_4)$-alkenyl, or
 (d) $(C_1-C_4)$-alkoxy-$C_1-C_4$-alkyl;

$R^{22}$ is:
 (a) CN,
 (b) $NO_2$, or
 (c) $COOR^{10}$; and

X is:
 (a) a carbon-carbon single bond,
 (b) $-CH_2-$,
 (c) $-CO-$,
 (d) $-O-$,
 (e) $-S(O)_x-$, (f) 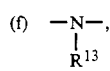

(g) 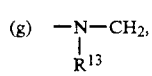

(h) 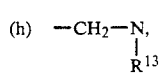

(i) 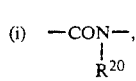

(j) 
$$-NCO-$$
$$\phantom{-N}|$$
$$\phantom{-NC}R^{20}$$

(k) $-OCH_2-$,
(l) $-CH_2O-$,
(m) $-S(O)_x-CH_2-$,
(n) $-CH_2S(O)_x-$,
(o) $-NHC(R^{10})(R^{20})$,
(p) $-NR^{10}SO_2-$,
(q) $-SO_2NR^{10}-$, or
(r) $-C(R^{10})(R^{20})NH-$;

and the pharmaceutically acceptable salts thereof.

One embodiment of the compounds of Formula I or those wherein:

$R^1$ is
 (a) $-CO_2R^{10}$,
 (b) $-PO(OR^{14})_2$,
 (c) $-NHSO_2R^{12}$,
 (d) $-SO_2NHR^{12}$, (e) 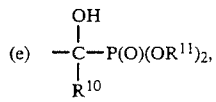

(f) 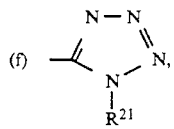

(g) 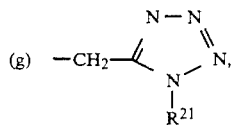

(h) 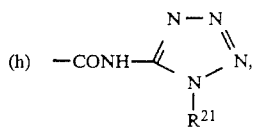

(i) $-CONHNHSO_2CF_3$, (j) 

(k) 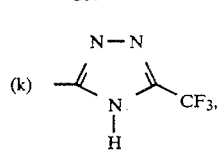

(l) 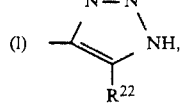

(m) $-CH_2SO_2NH-R^{12}$,
(n) $-SO_2NH-CO-R^{12}$,
(o) $-CH_2SO_2NH-CO-R^{12}$,
(p) $-CONH-SO_2R^{12}$,
(q) $-CH_2CONH-SO_2R^{12}$,
(r) $-NHSO_2NHCO-R^{12}$, (s) —NHCONHSO$_2$R$^{12}$,
(t) —SO$_2$NHCONR$^{2a}$R$^{12}$, or
(u) —CONHSO$_2$NR$^{2a}$R$^{12}$;

R$^3$ is
(a) —SO$_2$NH—R$^{12}$,
(b) —CH$_2$SO$_2$NH—R$^{12}$,
(c) —SO$_2$NHCO—R$^{12}$,
(d) —CH$_2$SO$_2$NHCO—R$^{12}$,
(e) —CONH—SO$_2$—R$^{12}$,
(f) —CH$_2$CONH—SO$_2$R$^{12}$,
(g) —NHSO$_2$NHCO—R$^{12}$,
(h) —NHCONHSO$_2$—R$^{12}$,
(i) —SO$_2$NHCONR$^{2a}$R$^{12}$, (j) 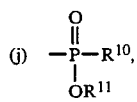

(k) —CONHSO$_2$NHCONR$^{2a}$R$^{12}$, or (l) 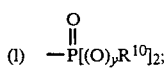

B is: a single bond or —S—;
R$^4$ is:
(a) H,
(b) (C$_1$–C$_6$)-alkyl, (C$_2$–C$_6$)-alkenyl or (C$_2$–C$_6$)-alkynyl,
(c) Cl, Br, I, F,
(d) NO$_2$,
(e) (C$_1$–C$_8$)-perfluoroalkyl,
(f) (C$_1$–C$_8$)-perfluoroalkenyl,
(g) pentafluorophenyl,
(h) CN,
(i) phenyl,
(j) phenyl-(C$_1$–C$_3$)-alkyl,
(k) phenyl and phenyl-(C$_1$–C$_3$)-alkyl substituted on the phenyl ring with one or two substituents selected from the group consisting of:
  i) (C$_1$–C$_4$)-alkyl,
  ii) (C$_1$–C$_4$)-alkoxyl,
  iii) F, Cl, Br, I,
  iv) hydroxyl,
  v) methoxyl,
  vi) CF$_3$,
  vii) CO$_2$R$^{2a}$,
  viii) NO$_2$, or
  ix) SO$_2$NR$^{2a}$R$^{2a}$,
(l) phenyl-(C$_2$–C$_6$)-alkenyl, (m) —C(=O)—R$^{16}$, (n) —(CH$_2$)$_n$—SO$_2$R$^{15}$ where n is 0–4,
(o) —(CH$_2$)$_m$-1,2,3-triazolyl, unsubstituted or substituted with one or two groups selected from:
  i) CO$_2$CH$_3$, or
  ii) (C$_1$–C$_4$)-alkyl, (p) —(CH$_2$)$_s$-[triazole ring]-CF$_3$, (q) —(CH$_2$)$_m$—N[piperazine]N-Aryl, or (r) —(CH$_2$)$_m$—N[piperazine]N-Heteroaryl;

R$^5$ is:
(a) (C$_1$–C$_9$)-alkyl, (C$_2$–C$_6$)-alkenyl or (C$_2$–C$_6$)-alkynyl each of which are unsubstituted or substituted with a substituent selected from the group consisting of:
  i) aryl, wherein aryl is defined as phenyl or naphthyl
  ii) (C$_3$–C$_7$)-cycloalkyl,
  iii) Cl, Br, I, F, or
  iv) CF$_3$, or
(b) (C$_1$–C$_4$)-perfluoroalkyl; and
X is a carbon-carbon single bond.

Illustrative of this embodiment are the following compounds:

TABLE 1

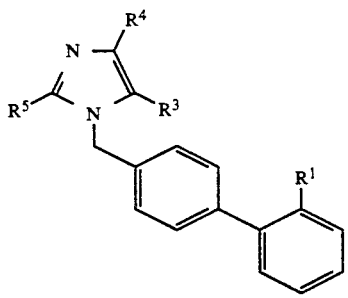

| Entry | R$^1$ | R$^3$ | R$^4$ | R$^5$ |
|---|---|---|---|---|
| 1. | —SO$_2$NHCOPh | —CONHSO$_2$Ph | Cl | n-butyl |
| 2. | —SO$_2$NHCO—◁ | —CONHSO$_2$Ph | Cl | n-butyl |

TABLE 1-continued

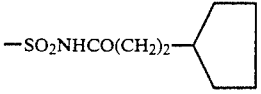

| Entry | R¹ | R³ | R⁴ | R⁵ |
|---|---|---|---|---|
| 3. | —SO₂NHCO(CH₂)₅—NH₂ | —CONHSO₂Ph | Cl | n-butyl |
| 4. | —SO₂—NHCO(CH₂)₄COOEt | —CONHSO₂Ph | Cl | n-butyl |
| 5. | 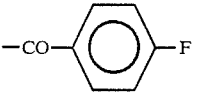 —SO₂NHCO(CH₂)₂-cyclopentyl | —CONHSO₂Ph | Cl | n-butyl |
| 6. | 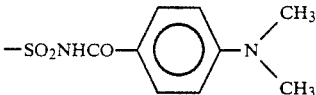 —SO₂—NH—CO—(4-F-C₆H₄) | —CONHSO₂Ph | Cl | n-butyl |
| 7. | 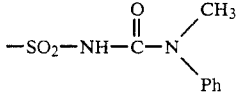 —SO₂NHCO—(4-N(CH₃)₂-C₆H₄) | —CONHSO₂Ph | Cl | n-butyl |
| 8. | —NHSO₂—NH—CO—Ph | —CONHSO₂Ph | Cl | n-butyl |
| 9. | 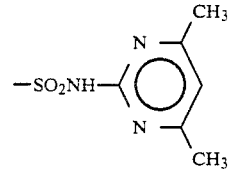 —SO₂—NH—C(O)—N(CH₃)(Ph) | —CONHSO₂Ph | Cl | n-butyl |
| 10. | 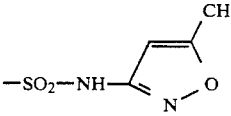 —SO₂NH—(4,6-dimethylpyrimidin-2-yl) | —CONHSO₂Ph | Cl | n-butyl |
| 11. | 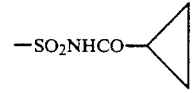 —SO₂—NH—(5-methylisoxazol-3-yl) | —CONHSO₂Ph | Cl | n-butyl |
| 12. | —COOH | —CONHSO₂Ph | Cl | n-butyl |
| 13. | tetrazol-5-yl | —CONHSO₂Ph | Cl | n-butyl |
| 14. | tetrazol-5-yl | —SO₂NHCOPh | Cl | n-butyl |
| 15. | tetrazol-5-yl | —SO₂NHCO-cyclopropyl | Cl | n-propyl |
| 16. | 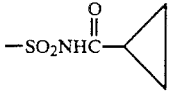 —SO₂NHC(O)-cyclopropyl | —SO₂NHCOPh | ethyl | n-propyl |
| 17. | tetrazol-5-yl | 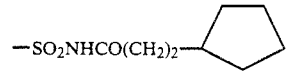 —SO₂NHCO(CH₂)₂-cyclopentyl | ethyl | n-propyl |

TABLE 1-continued

| Entry | R¹ | R³ | R⁴ | R⁵ |
|---|---|---|---|---|
| 18. | tetrazol-5-yl | —SO₂NHCO(CH₂)₂-cyclopentyl | Cl | n-propyl |
| 19. | —SO₂NHCOPh | —SO₂NHCO(CH₂)₂-cyclopentyl | ethyl | n-propyl |
| 20. | —SO₂NHCO-cyclopropyl | —SO₂NHCO(CH₂)₅NH₂ | ethyl | n-propyl |
| 21. | —SO₂NHCO-cyclopropyl | —SO₂NHCO(CH₂)₅NH₂ | H | n-propyl |
| 22. | —SO₂NH—COPh | —SO₂NHCO(CH₂)₅NH₂ | H | n-butyl |
| 23. | —SO₂NH—COPh | —CONHSO₂Ph | ethyl | n-propyl |
| 24. | —SO₂—NHCO(CH₂)₅NH₂ | —COOCH₂—O—C(=O)—CH₃ | ethyl | n-propyl |
| 25. | tetrazol-5-yl | —SO₂NH-(4,6-dimethylpyrimidin-2-yl) | Cl | n-butyl |
| 26. | tetrazol-5-yl | —SO₂NH-(4,6-dimethylpyrimidin-2-yl) | H | n-butyl |
| 27. | tetrazol-5-yl | —SO₂NH-(4,6-dimethylpyrimidin-2-yl) | Cl | n-propyl |
| 28. | —SO₂NHCOPh | —SO₂NH-(4,6-dimethylpyrimidin-2-yl) | Cl | n-propyl |

TABLE 1-continued

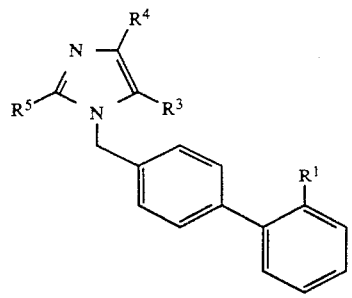

| Entry | R¹ | R³ | R⁴ | R⁵ |
|---|---|---|---|---|
| 29. | —NHSO$_2$NHCOPh | —CONHSO$_2$Ph | Cl | n-propyl |
| 30. | —NHSO$_2$NHCOPh | —CONHSO$_2$Ph | ethyl | n-propyl |
| 31. | —SO$_2$NHCOPh | —SO$_2$NHCOPh | CF$_2$CF$_3$ | n-propyl |

GENERAL METHODS FOR PREPARATION OF COMPOUNDS OF GENERAL FORMULA I

The methods described below illustrate the preparation of angiotensin II antagonists of Formula I. There are several general approaches to the synthesis of antagonists of Formula I, and it is taken as a general principle that one or another method may be more readily applicable for the preparation of a given antagonist; some of the approaches illustrated below may not be readily applicable for the preparation of certain antagonists of Formula I.

Abreviations used in the following schemes and examples are listed below:

| Reagents | |
|---|---|
| NBS | N-bromosuccinimide |
| AIBN | Azo(bis)isobutyronitrile |
| Ac$_2$O | acetic anhydride |
| TEA | triethylamine |
| DMAP | 4-dimethylaminopyridine |
| PPh$_3$ | triphenylphosphine |
| TFA | trifluoroacetic acid |
| TMS-Cl | trimethylsilyl chloride |
| p-TsOH | p-toluenesulfonic acid |
| DIPEA | Diisopropylethylamine |
| TBAF | tetrabutylammonium fluoride |
| Solvents: | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| Others: | |
| rt | room temperature |
| TBDMS | t-butyldimethylsilyl |
| OTf | OSO$_2$CF$_3$ |
| Ph | phenyl |
| FAB-MS (FSBMS) | Fast atom bombardment mass spectroscopy |
| NOE | Nuclear Overhauser Effect |
| SiO$_2$ | silica gel |
| trityl | triphenylmethyl |

As shown in Scheme 1, compounds of Formula I can be prepared by carrying out direct alkylation of alkalimetal salts of imidazole derivatives (1) (preparation of imidazole derivatives are described in European Patent Applications 253,310 and 324,377, and also in Comprehensive Heterocyclic Chemistry, Vol. 5, part 4A, pages 345–498 which are incorporated herein by reference thereto) using appropriately protected benzyl halide, tosylate (OTs) or mesylate (OMs) derivatives (2). The salt is prepared preferably using MH (where M is lithium, sodium or potassium) in anhydrous dimethylformamide (DMF), or by treating it with a metal alkoxide such as sodium or potassium methoxide, ethoxide or t-butoxide in an appropriate alcohol such as methanol, ethanol or t-butanol as the solvent. The alkylation is generally carried out by dissolving the metal salt of the heterocycle in a dipolar aprotic solvent such as DMF or dimethylsulfoxide (DMSO) and reacting it with the alkylating agent at 20° C. to reflux temperature of the solvent for 1–24 hours.

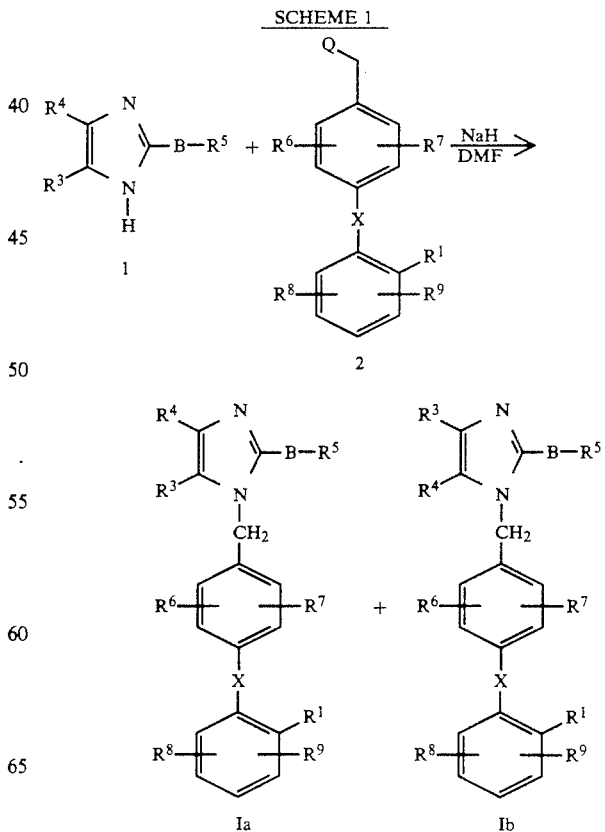

SCHEME 1 where Q=halo(I, Br, Cl), —O—tosyl, —O—mesyl

If substituents on the imidazole ring are not symmetrically disposed, the alkylation on the imidazole nitrogen(s) generally produces a mixture of two regioisomers as products arising from $N^1$ and $N^3$ alkylation. These regioisomers Ia and Ib possess distinct physicochemical and biological properties and in most cases can be separated and purified by using conventional separation techniques such as chromatography (flash column chromatography, medium-pressure liquid chromatography, high performance liquid chromatography) and/or crystallization. In those cases where separation of regioisomers is difficult by conventional techniques, the mixture can be transformed into suitable derivatives that can be separated by the above separation methods. The structural assignments of the isomers can be made using Nuclear Overhauser Effect (NOE), $^1H$—$^{13}C$ coupled NMR experiments or X-ray crystallography.

The biphenyl precursors 7a, 7b, 7c and 7d required for the synthesis of substituted benzyl halides (2) may be preferably prepared using Ni(0) or Pd(0) catalyzed cross-coupling reaction [E. Negishi, T. Takahashi, and A. O. King, Org. Synthesis, 66, 67 (1987)] as is outlined in Scheme 2. As shown in Scheme 2, treatment of 4-bromotoluene (3) with t-BuLi, followed by the addition of a solution of $ZnCl_2$, produces the organo-zinc compound (5). Compound (5) is then coupled with 6a, 6b, 6c or 6d in the presence of $Pd(PPh_3)_4$ or $Ni(PPh_3)Cl_2$ catalyst to produce the desired biphenyl compound 7a, 7b, 7c or 7d, respectively. The cyano biphenyl intermediate 7d is converted into the protected tetrazoyl precursor 7e according to procedures described in European Patent Application 253,310 and 292,969. These precursors (7a-7e) are then transformed into bromomethylbiphenyl derivatives 8a-8e, respectively, by reacting them with N-bromosuccinimide in the presence of AIBN or benzoylperoxide in refluxing carbontetrachloride.

When there are additional substituents on the second phenyl ring ($R^8$ and $R^9$ are not hydrogen) the preferred method to prepare the biphenyl precursors 11 using the Pd(0) catalyzed cross-coupling reaction [J. K. Stille, Angew, Chem. Int. Ed. Engl., 25, 508 (1986)], is outlined in Scheme 3. As shown in Scheme 3, p-tolyltrimethyltin (9) is reacted with 10 in refluxing toluene in the presence of 5 mole % of $Pd(PPh_3)_4$ or in dry DMF in the presence of $Pd(PPh_3)_2Cl_2$ at 90° C. to produce the desired biphenyl compounds 11. Compounds 11 bearing $R^8$ or $R^9$ as $NO_2$ groups could be converted to their respective chlorides by catalytic hydrogenation, diazotization and treatment with copper (I) chloride. Similarly, the biphenyl fluorides which could not be obtained by direct coupling to a fluoroarylbromide precursor (10) were prepared from the corresponding nitro compound via reduction, formation of the diazonium tetrafluoroborate salt and thermal decomposition. These precursors 11 are then transformed into the halomethyl biphenyl derivatives 12 according to the procedures described in European Patent Applications 253,310 and 292,969.

SCHEME 2

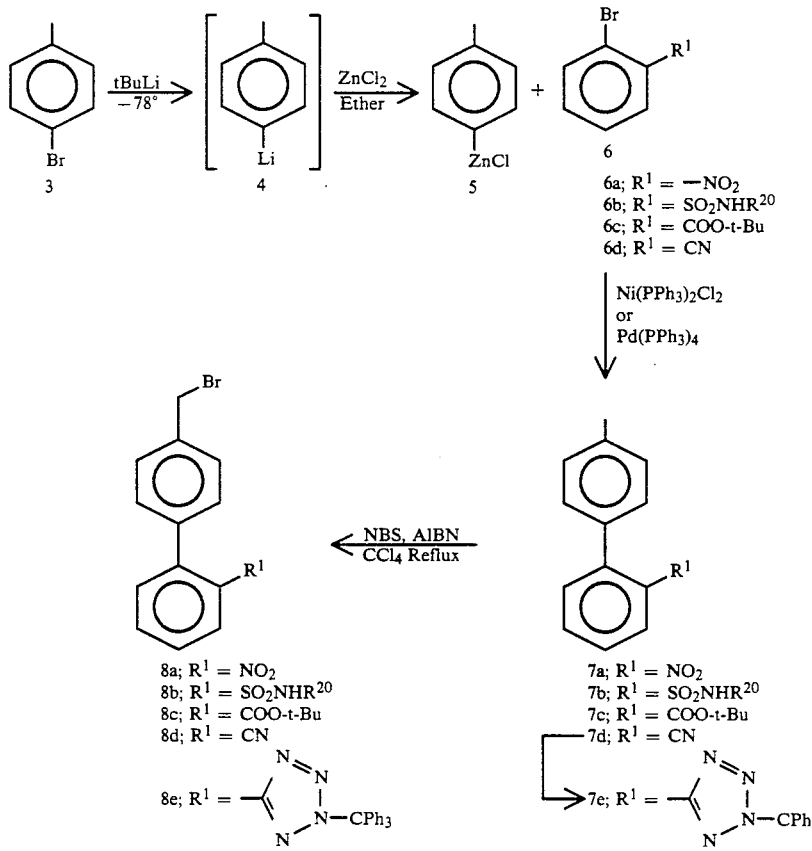

6a; $R^1$ = —$NO_2$
6b; $R^1$ = $SO_2NHR^{20}$
6c; $R^1$ = COO-t-Bu
6d; $R^1$ = CN

8a; $R^1$ = $NO_2$
8b; $R^1$ = $SO_2NHR^{20}$
8c; $R^1$ = COO-t-Bu
8d; $R^1$ = CN

8e; $R^1$ = tetrazole-N—$CPh_3$

7a; $R^1$ = $NO_2$
7b; $R^1$ = $SO_2NHR^{20}$
7c; $R^1$ = COO-t-Bu
7d; $R^1$ = CN

7e; $R^1$ = tetrazole-N—$CPh_3$

SCHEME 3

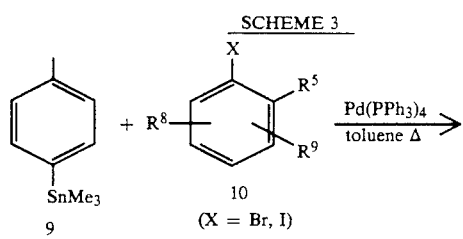

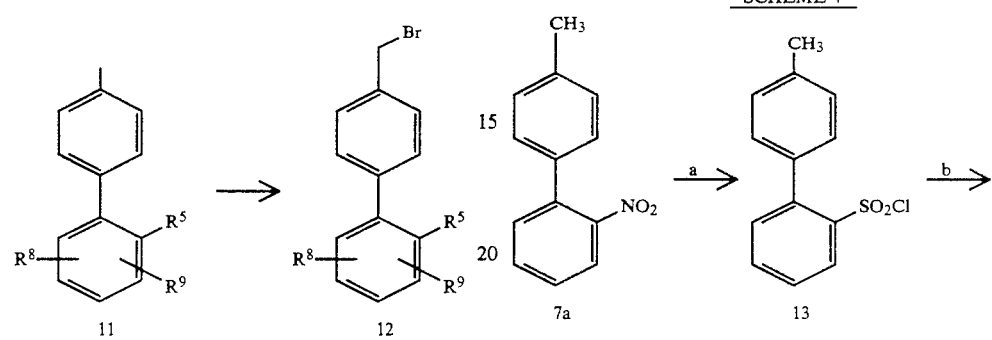

alkali metal salt of an appropriate imidazole derivative to form the key sulfonamide 17. The sulfonamide 17 may be also prepared from the aromatic sulfonyl chloride 22, which may be prepared from the aryl amine 21 as outlined in Scheme 5. The acylation of 17 with appropriate acyl chlorides (or acyl-imidazoles or other acylating agents) may produce the desired acylsulfonamides 18.

SCHEME 4

TABLE I
Biphenyl Synthesis

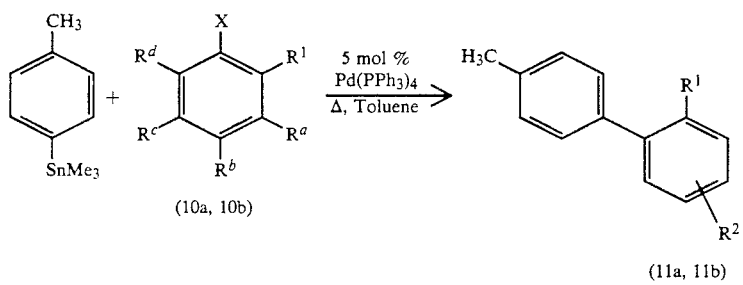

| X | $R^1$ | $R^a$ | $R^b$ | $R^c$ | $R^d$ | Product ($R^2$) | Rf (solvent) | Yield |
|---|---|---|---|---|---|---|---|---|
| Br | $CO_2Me$ | $NO_2$ | H | H | H | 11a (3'-nitro) | 0.35 (15:1 Hex/EtOAc) | 71% |
| Br | CN | H | $NO_2$ | H | H | 11b (4'-nitro) | 0.62 (2 × 6:1 Hex/EtOAc) | 74% |
| Br | $CO_2Me$ | H | F | H | H | 11a (4'-fluoro) | 0.43 (15:1 Hex/EtOAc) | 83% |
| Cl | $CO_2Me$ | H | H | $NO_2$ | H | 11a (5'-nitro) | 0.22 (15:1 Hex/EtOAc) | 70% |
| Br | $CO_2Me$ | H | H | H | $NO_2$ | 11a (6'-nitro) | 0.24 (15:1 Hex/EtOAc) | 79% |
| Br | CN | H | F | H | H | 11b (4'-fluoro) | 0.44 (15:1 Hex/EtOAc) | 64% |
| Cl | CN | H | H | F | H | 11b (5'-fluoro) | 0.40 (15:1 Hex/EtOAc) | 62% |

Compounds of formula I where $R^1$ is $-SO_2NHCOR^{12}$ may be prepared as outlined in Scheme 4. The nitro compound 7a (prepared as described in Scheme 2) can be reduced to the corresponding amino compound and converted into aromatic diazonium chloride salt, which then can be reacted with sulfur-dioxide in the presence of a copper(I) salt to form the corresponding arylsulfonylchloride 13 [H. Meerwein, G. Dittmar, R. Gollner, K. Hafner, F. Mensch and O. Steifort—*Chem. Ber.*, 90, 841 (1957); A. J. Prinsen and H. Cerfontain, *Recueil*, 84, 24 (1965); E. E. Gilbert, *Synthesis*, 3 (1969) and references cited therein]. The sulfonyl chloride can be reacted with ammonia in aqueous solution or in an inert organic solvent [F. H. Bergheim and W. Baker, *J. Amer. Chem. Soc.*, 66, (1944), 1459], or with dry powdered ammonium carbonate, [E. H. Huntress and J. S. Autenrieth, *J. Amer. Chem. Soc.*, 63, (1941), 3446; E. H. Huntress and F. H. Carten, *J. Amer. Chem. Soc.*, 62, (1940), 511] to form the sulfonamide 14. The benzylbromide 16 may be prepared from the sulfonamide 14 as outlined in Scheme 4, and then can be reacted with an

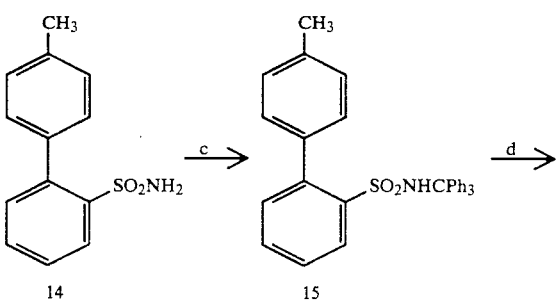

-continued
SCHEME 4

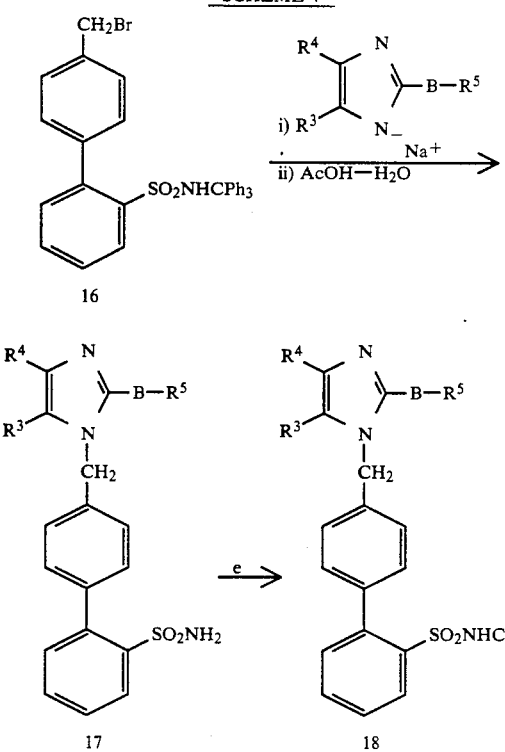

a. i) H₂/Pd—C, ii) NaNO₂—HCl, iii) SO₂, AcOH, CuCl₂
b. NH₃ or (NH₄)₂CO₃
c. Ph₃CCl, NaH, DMF
d. N-bromosuccinimide
e. R¹²COCl or R¹²CO—Im or other acylating agents.

The compounds (23) bearing R¹ as —SO₂NHR¹² (where R¹² is heteroaryl) may be prepared by reacting the aromatic sulfonyl chloride 22 with appropriate heteroaryl amines as outlined in Scheme 5. The sulfonyl chloride 22 may be the preferred intermediate for the synthesis of this class of compounds. The aromatic sulfonyl chlorides may also be prepared by reacting the sodium salt of aromatic sulfonic acids with PCl₅ or POCl₃ [C. M. Suter, *The organic Chemistry of Sulfur*, John Wiley & sons, 459, (1944)]. The aromatic sulfonic acid precursors may be prepared by chlorosulfonation of the aromatic ring with chlorosulfonic acid [E. H. Huntress and F. H. Carten, *J. Amer. Chem. Soc.*, 62, 511 (1940)].

SCHEME 5

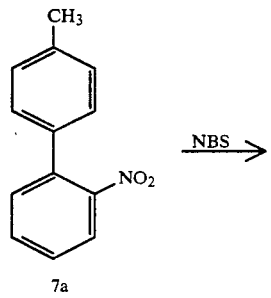

-continued
SCHEME 5

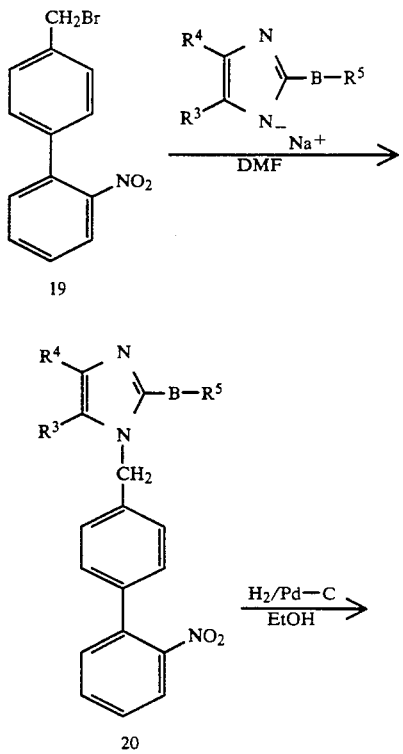

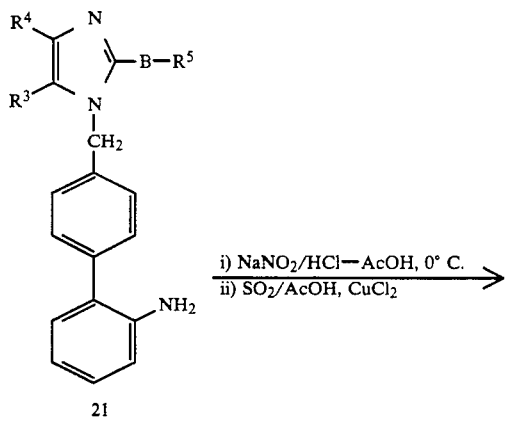

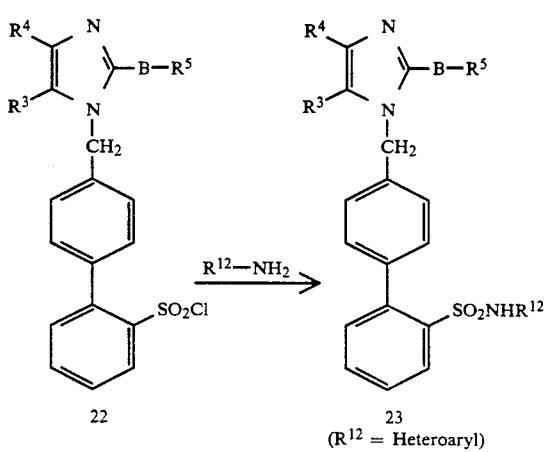

5,236,928
SCHEME 6
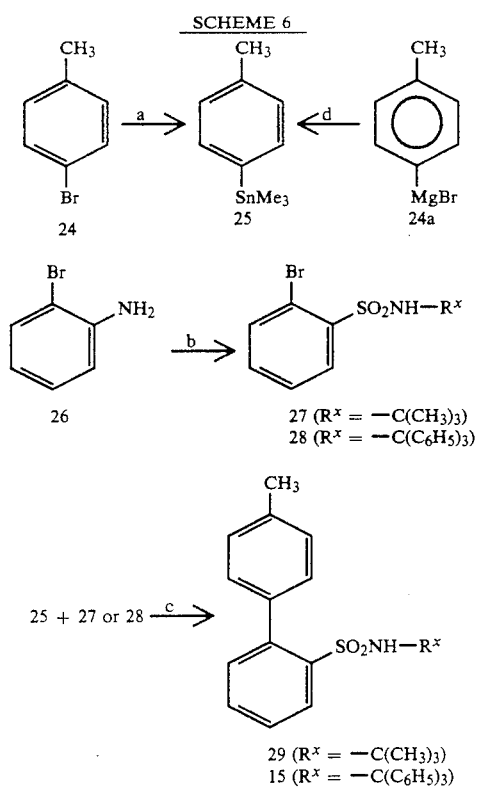
a. t-BuLi/ether, −78° C.
b. i) NaNO₂/HCl ii) SO₂, CuCl₂
   iii) t-butylamine, or NH₃ and then Ph₃CCl
c. Pd(PPh₃)₄, toluene or (PPh₃)₂PdCl₂, DMF, 90° C.
d. Me₃SnCl.
SCHEME 7
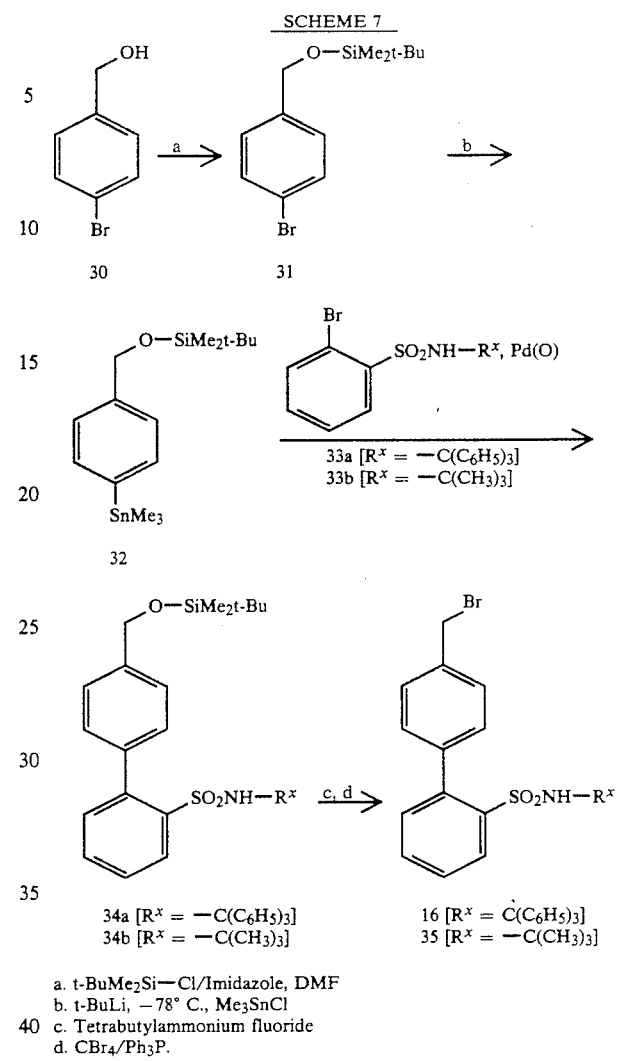
a. t-BuMe₂Si—Cl/Imidazole, DMF
b. t-BuLi, −78° C., Me₃SnCl
c. Tetrabutylammonium fluoride
d. CBr₄/Ph₃P.
SCHEME 8
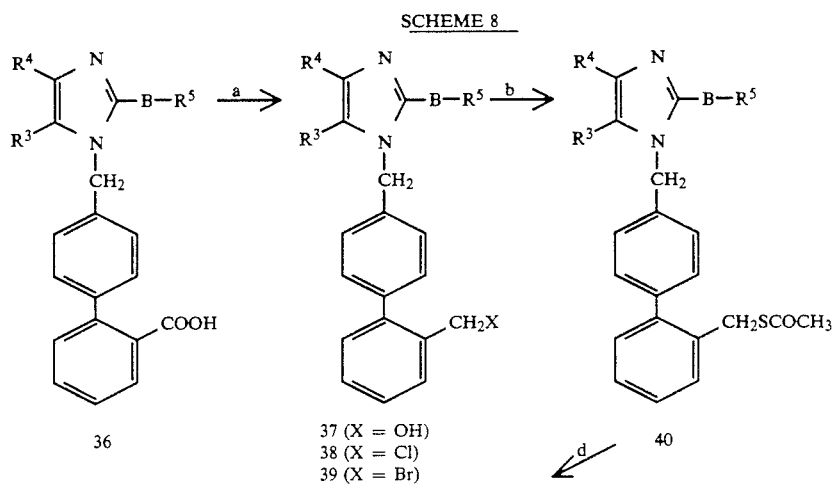

SCHEME 8
-continued
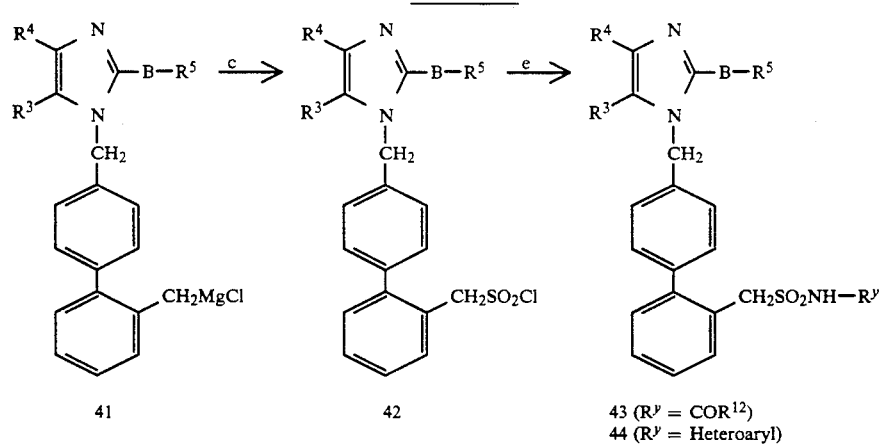
a. i) EtOCOCl/Et₃N, THF, 0° C. ii) NaBH₄ iii) CCl₄ or CBr₄/PPh₃
b. AcSk
c. SO₂Cl₂
d. Cl₂, AcOH, H₂O or, i) SO₂Cl₂ ii) oxidation
e. R$^y$NH₂ or, i) NH₃ ii) Acylation
SCHEME 9
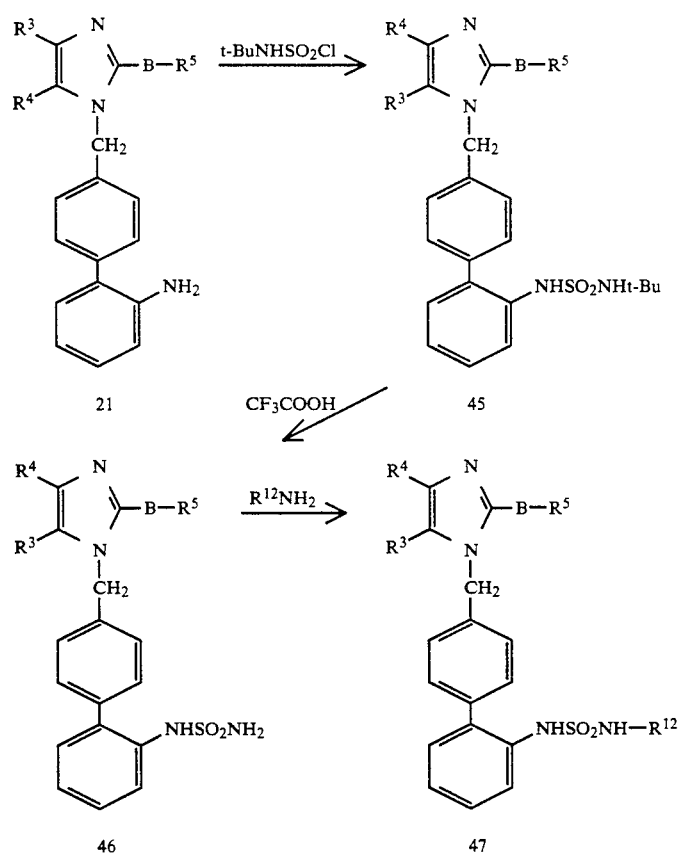

SCHEME 10

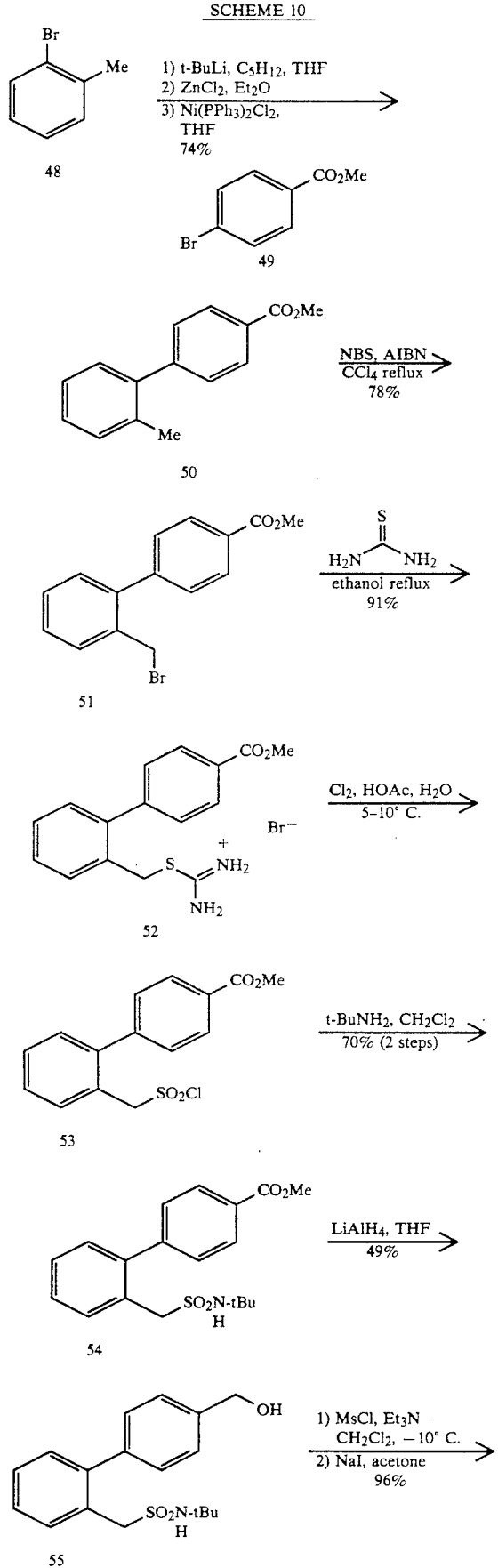

-continued
SCHEME 10

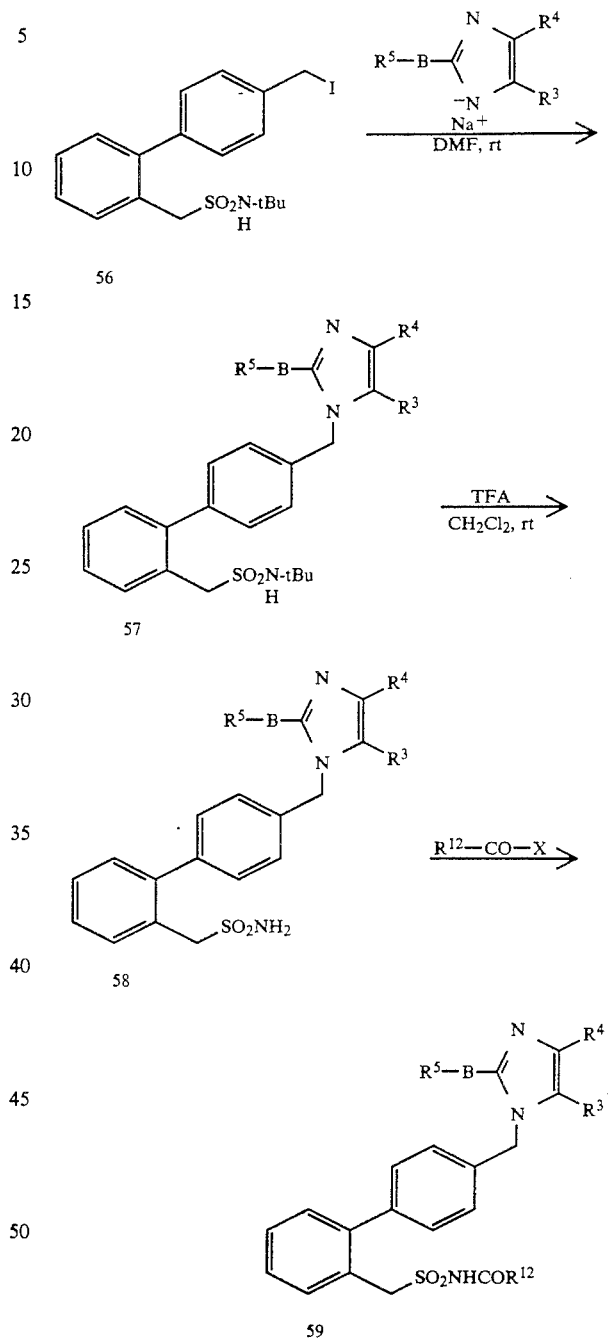

The biaryl sulfonamides 29 and 15 can be prepared alternatively using palladium(0) catalyzed cross-coupling reactions of appropriate aryl-organotin precursors [J. K. Stille, *Pure Appl. Chem.*, 57, 1771 (1985); T. R. Bailey, *Tetra Lett.*, 27, 4407 (1986); D. A. Widdowson and Y. Z. Zhang, *Tetrahedron*, 42, 2111 (1986)], as outlined in Scheme 6. The organotin compound 25 [S. M. Moerlein, *J. Organometallic Chem.*, 319, 29 (1987)], obtained from the aromatic precursor 24 or 24a, may be coupled with aryl sulfonamides 27 and 28 using Pd(PPh$_3$)$_4$ or (PPh$_3$)$_2$PdCl$_2$ as catalysts to give biaryl sulfonamides 29 and 15, respectively. Similarly, the benzyl bromides 16 and 35 may be alternatively prepared from the appropriate organotin precursor 32 using the Pd(O) catalyzed cross-coupling reaction as outlined in Scheme 7.

The compounds bearing $R^1$ as $-CH_2SO_2NHCOR^{12}$ and $-CH_2SO_2NHR^{12}$ may be prepared as outlined in Scheme 8. The key precursor aryl-methanesulfonyl chloride 42 may be prepared either from the reaction of aryl-methylmagnesium chloride (41) (obtained from the corresponding benzyl chloride (38)) with sulfurylchloride [S. N. Bhattacharya, C. Eaborn and D. P. M. Walton, *J. Chem. Soc.* C, 1265 (1968)], or by oxidation of the aryl-methylthioacetate (40) (prepared from the benzyl bromide 39) with chlorine in presence of trace amount of water [Bagnay and Dransch, *Chem. Ber.*, 93, 784 (1960)]. Alternatively, the aryl-methylthioacetate (40) may be oxidized with sulfuryl chloride in presence of acetic anhydride to form aryl-methylsulfinyl chloride [S. Thea and G. Cevasco, *Tetra. Lett.*, 28, 5193 (1987)], which can be further oxidized with appropriate oxidizing agents to give the sulfonyl chloride 42. The compounds 43 and 44 can be obtained by reacting the sulfonyl chloride 42 with appropriate amines or with ammonia followed by acylation.

Compounds where $R^1 = -NHSO_2NHR^{12}$ may be prepared by the reaction of appropriate primary amines with the sulfamide 46 [S. D. McDermott and W. J. Spillane, *Synthesis*, 192 (1983)], as described in Scheme 9. The compound 46 may be obtained from the corresponding N-t-butylsulfamide 45 after treatment with anhydrous trifluoroacetic acid [J. D. Catt and W. L. Matier, *J. Org. Chem.*, 39, 566 (1974)], which may be prepared by the reaction of the aromatic amine 21 with t-butylsulfamoyl chloride [W. L. Matier, W. T. Comer and D. Deitchman, *J. Med. Chem.*, 15, 538 (1972)].

Antagonists of Formula I in which $R^1 = -CH_2SO_2NHCOR^{12}$ may be prepared as illustrated in Scheme 10. 2-Bromotoluene (48) is treated with t-butyllithium and then zinc chloride. Coupling of the resulting metallo-zinc species with 4-bromobenzoic acid methyl ester (49) is then carried out with bis(triphenylphosphine)nickle(II) chloride as catalyst. Bromination of the resulting biphenyl (50) is then carried out using N-bromosuccinimide, affording bromide 51. Treatment of the bromide with thiourea affords the salt 52 which is treated with chlorine to yield sulfonyl chloride 53. Treatment of 53 with t-butylamine affords sulfonamide 54, which is converted by treatment with lithium aluminum hydride to the alcohol 55. Conversion of 55 to the corresponding iodide 56 is carried out by treatment with methanesulfonyl chloride to afford a sulfonate ester, followed by treatment with sodium iodide in acetone. The iodide 56 is used to alkylate the sodium salt of an appropriate heterocyclic compound, affording the sulfonamide 57. Treatment of 57 with trifluoroacetic acid then affords the sulfonamide analog 58, which on further treatment with an appropriate acylating agent affords the desired acylsulfonamides 59.

-continued
SCHEME 11

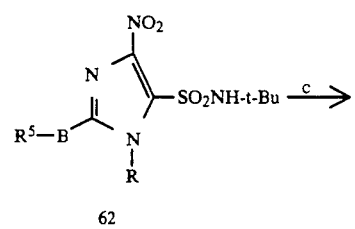
62

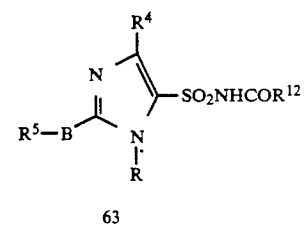
63

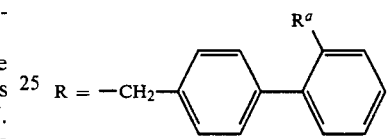

$R^a$ = A precursor group for $R^1$
a. $H_2S$, $NH_4OH$, 25° C.
b. (i) $Cl_2$, Conc.HCl, $H_2O$, 25° C., (ii) t-butylamine, $CHCl_3$
c. (i) TFA, 25° C., (ii) aqueous $NaHCO_3$,
 (iii) $R^{12}CO$-imidazole, DBU, THF or
 $R^{12}COCl$, pyridine, DMAP(cat.).

SCHEME 12

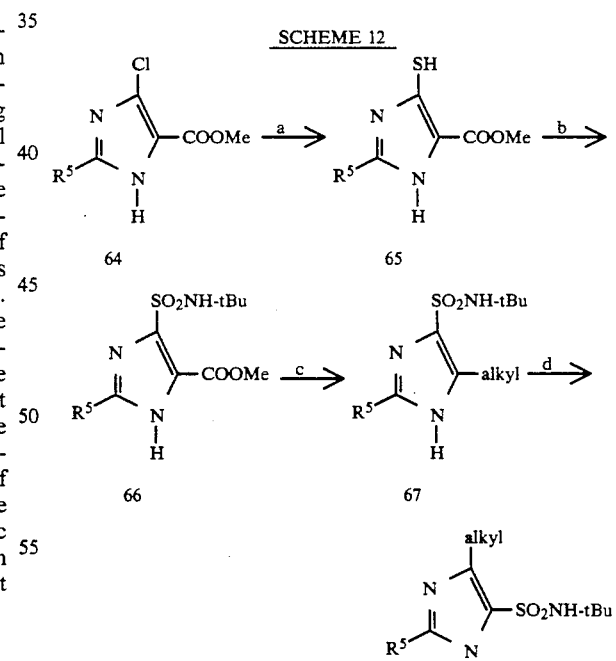

SCHEME 11

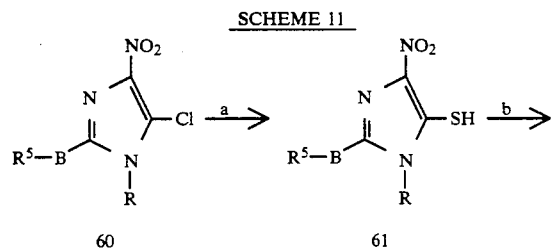

-continued
SCHEME 12

$R^a$ = precursor of $R^1$
a. (i) NaSH, CH$_3$OH—H$_2$O, (ii) H$_3$O$^+$
b. (i) Cl$_2$, Conc.HCl, H$_2$O, 25° C., (ii) t-Butylamine
c. (i) LiAlH$_4$, THF, (ii) MnO$_2$, CH$_2$Cl$_2$, 25° C.;
 (iii) R$^b$—CH=PPh$_3$, (iv) H$_2$/Pd—C.
d. (i) NaH or K$_2$CO$_3$, DMF,

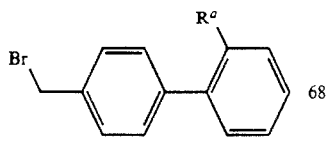

68

SCHEME 13

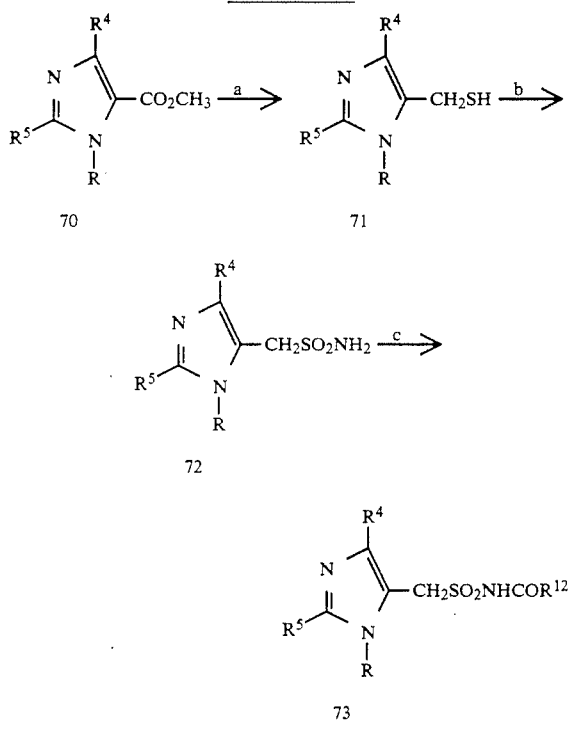

a. (i) H$_2$S, NH$_4$OH
b. 51) Cl$_2$, Conc.HCl, H$_2$O, 25° C., (ii) NH$_3$, CHCl$_3$
c. (i) R$^{12}$CO-imidazole, DBU, THF or (ii) R$^{12}$COCl, pyridine, DMAP (cat.)

SCHEME 14

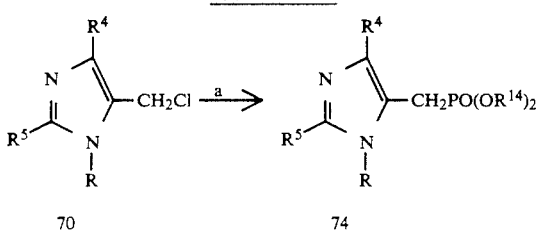

-continued
SCHEME 14

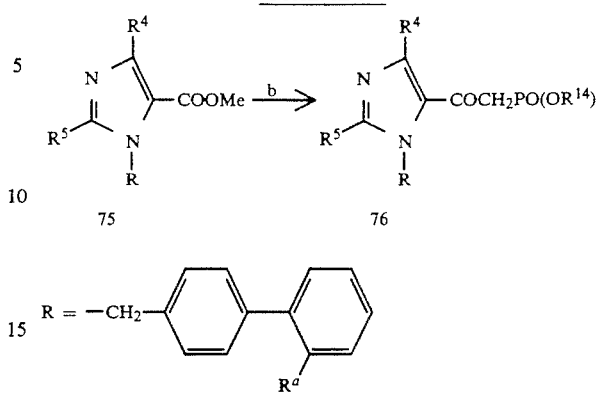

a. P(O-alkyl)$_3$, reflux
b. CH$_3$—PO(OR$^{14}$), n-BuLi, THF, −78° C.

SCHEME 15

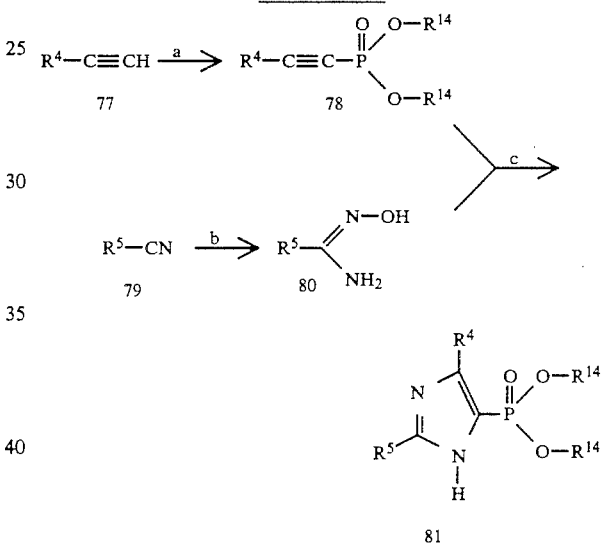

a. (i) LiN(i-Pr)$_2$, THF, −78° C., (ii) Cl—P(O)(OR$^{14}$)$_2$
b. NH$_2$—OH.HCl, NaOMe, MeOH, reflux
c. xylene, reflux Compounds of formula I where $R^5$=—SO$_2$NH-COR$^{12}$ may be prepared from the 5-chloro-4-nitro imidazole derivative 60 as outlined in Scheme 11. The starting intermediate 60 may be prepared by the alkylation of 5-chloro-4-nitro imidazole [L. L. Bennett and H. T. Baker, J. Am. Chem. Soc. 79, 2188 (1957)] with an appropriate biphenyl methyl bromide (68) as described in Scheme 1, the resulting product may then be transformed into the corresponding thiol 61. The oxidative chlorination of 61 under acidic condition may form the corresponding sulfonyl chloride [F. F. Blicke and C. M. Lee, J. Org. Chem., 26 1861, (1961); M. H. Fisher, W. H. Nicholson, and R. S. Stuart, Cand. J. Chem., 39, 501, (1961)] which upon treatment with t-butylamine may produce the sulfonamide 62. Treatment of 62 with appropriate acylating agents may furnish the desired acylsulfonamides 63. Analogues of 63 (where R$^4$ is alkyl) may be prepared from the intermediate 69 which may be prepared as illustrated in Scheme 12. The thiol 65 obtained from 64 can be oxidized, and the resulting sulfonyl chloride may then be treated with t-butylamine to form 66. Transformation of the ester function in 66 into an appropriate alkyl group may produce compound 67, which can be alkylated with 68 to provide the desired intermediate 69.

Analogues of formula I where $R^5=-CH_2SO_2NH-COR^{12}$ may be prepared from the intermediate 70 as outlined in Scheme 13. The sulfonamide 72 (prepared from the thiol 71 as described) may be reacted with appropriate acylating agents to give antagonists 73.

Compounds of formula I where $R^5-CH_2PO(OR^{14})_2$ also may be prepared from an imidazole intermediate 70. The Arbuzov reaction of 70 with an appropriate trialkyl phosphite can produce the phosphonate 74 (Scheme 14). Similarly, the keto phosphonate antagonist 76 may be prepared by the reaction of anion of an appropriate methylphosphonate with an imidazole-5-carboxylate (75) as shown in Scheme 14.

Antagonists of formula I where $R^5$ is $-PO(OR^{14})_2$ may be prepared from an imidazole precursor 81 (Scheme 15). Claisen rearrangement of the adduct formed when an acetylenic compound 78 and an amidoxime (79) are combined may lead to imidazole-5-phosphonate (81) [M. R. Grimmett, Adv. Heterocycl. Chem., 27, 241 (1980)].

SCHEME 16

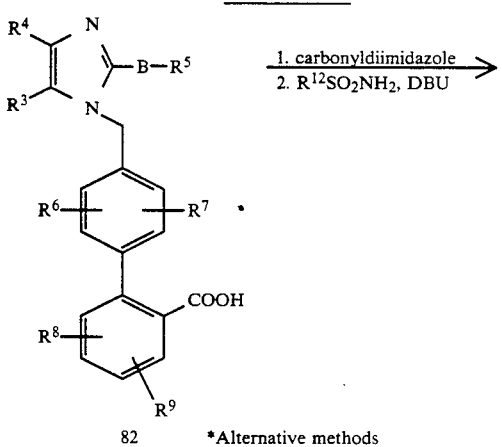

82   *Alternative methods

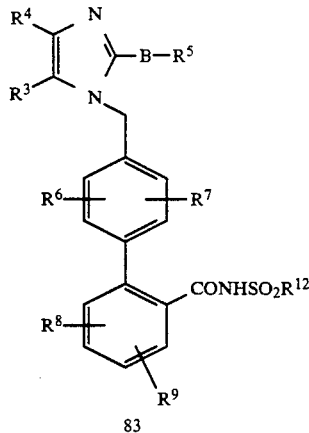

83

*Alternative Methods:

a) (i) SOCl₂, reflux;
   (ii) $R^{12}SO_2N^-M^+$ (where M is Na or Li
b) (i) (COCl)₂—DMF, −20° C.
   (ii) $R^{12}SO_2N^-M^+$ -continued
SCHEME 16 c) (i) N-(N,N-diphenylcarbamoyl)pyridinium chloride/aq. NaOH
   (ii) $R^{12}SO_2N^-M^+$.

Compounds of formula I where $R^1$ is $-CONHSO_2R^{12}$ (where $R^{12}=$alkyl, aryl or heteroaryl) may be prepared from the corresponding carboxylic acid derivatives (82) as outlined in Scheme 16. The carboxylic acid 82, obtained as described in Scheme 1, can be converted into the corresponding acid chloride by treatment with refluxing thionyl chloride or preferably with oxalyl chloride and a catalytic amount of dimethylformamide at low temperature [A. W. Burgstahler, L. O. Weigel, and C. G. Schaefer—Synthesis, 767, (1976)]. The resulting acid chloride then can be treated with the alkali metal salt of $R^{12}SO_2NH_2$ to form the desired acylsulfonamide 83. Alternatively, these acylsulfonamides may be also prepared from the carboxylic acids using N,N-diphenylcarbamoyl anhydride intermediates [F. J. Brown, et al.—European Patent Application 199,543; K. L. Shepard and W. Halczenko—J. Het. Chem., 16, 321 (1979)]. Preferably the carboxylic acids can be converted into acyl-imidazole intermediates, which then can be treated with the appropriate aryl or alkylsulfonamide and diazabicycloundecene (DBU) to give the desired acylsulfonamide 83 [J. T. Drummond and G. Johnson, Tetra. Lett., 29, 1653 (1988)]. Compounds of the Formula I where $R^3$ is $CONHSO_2R^{12}$ may also be prepared from the corresponding imidazole-5-carboxylic acid compounds (where $R^3=CO_2H$) as described above.

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkai metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, H₂SO₄, H₃PO₄, methane-sulfonic, toluensulfonic, maleic, fumaric, camphorsulfonic. The nontoxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor Binding Assay Using Rabbit Aortae Membrane Preparation

Three frozen rabbit aortae (obtained from Pel-Freeze Biologicals) were suspended in 5 mM Tris-0.25M Sucrose, pH 7.4 buffer (50 ml) homogenized, and then centifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitration and the suspension was used for 100 assay tubes. Samples tested for screening were done in duplicate. To the membrane preparation (0.25 ml) there was added $^{125}I$-$Sar^1Ile^8$-angiotensin II [obtained from New England Nuclear] (10 ul; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}I$-$Sar^1Ile^8$-angiotensin II was presented as a measure of the efficacy of such compounds as AII antagonists.

Receptor Assay Using Bovine Adrenal Cortex Preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF) (0.1 mM)]. (For screening of compounds, generally duplicates of tubes are used). To the membrane preparation (0.5 ml) there was added 3H-angiotensin II (50 mM) (10 ul) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^3H$-angiotensin II was presented as a measure of the efficacy of such compounds as AII antagonists.

Using the methodology described above, representative compounds of the invention were evaluated and were found to exhibit an activity of at least $IC_{50} < 50$ $\mu M$ thereby demonstrating and confirming the utility of the compounds of the invention as effective AII antagonists.

The potential antihypertensive effects of the compounds described in the present invention may be evaluated using the methodology described below: Male Charles River Sprague-Dawley rats (300–375 gm) were anesthetized with methohexital (Brevital; 50 mg/kg i.p.). The trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volumn—1.1 cc per 100 grams body weight). The right carotid artery was ligated, both left and right vagal nerves were cut, the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered and 15 minutes later propranolol (1 mg/kg i.v.). Thirty minutes later antagonists of formula I were administered intravenously or orally. Angiotensin II was then typically given at 5, 10, 15, 30, 45 and 60 minute intervals and every half-hour thereafter for as long as the test compound showed activity. The change in the mean arterial blood pressure was recorded for each angiotensin II challenge and the percent inhibition of the angiotensin II response was calculated.

Thus, the compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinapathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of Formula I and their incorporation into pharmaceutical compositions and as such are not to be considered nor construed as limiting the invention set forth in the claims appended hereto.

EXAMPLE 1

Preparation of 4'-bromomethylbiphenyl-2-t-butylsulfonamide

Step 1: Preparation of 2-bromobenzene-(tertsulfonamide

To a stirred solution of 2-bromobenzenesulfonyl chloride (Lancaster Synthesis) (2.21 g, 8.65 mmol) in chloroform (40 ml) under nitrogen at room temperature was added tert-butylamine (Aldrich) (2.30 ml, 21.9 mmol). The orange solution was stirred at room temperature for 12 hours, then the mixture evaporated to dryness. Flash chromatography (silica gel, 15% ethyl acetate-hexane) afforded 2-bromobenzene(tert-butyl)sulfonamide (2.12 g, 84%) as a white solid; $^1$H NMR (300 MHz, CDCl$_3$) $\delta$8.18 (d, J=8.5 Hz, 1H), 7.73 (d, J=8.5 Hz, 1H), 7.50-7.35 (m, 2H), 5.11 (s, 1H), 1.20 (s, 9H).

Step 2: Preparation of p-tolyltrimethyltin p-Tolylmagnesium bromide solution (Aldrich) (1.0M solution in diethyl ether) (53 ml, 0.0530 mol) was added dropwise to trimethyltin chloride (6.92 g, 0.0347 mol) in tetrahydrofuran (50 ml) under nitrogen at −10° C. The suspension was allowed to warm slowly to room temperature over 3 hours then saturated ammonium chloride solution (10 ml) was added followed by sufficient water to dissolve the precipitate. The solution was extracted three times with diethyl ether-hexane (1:1). The combined organic phase was washed with brine, dried (magnesium sulfate) and the solvents removed in vacuo. Vacuum distillation of the residue afforded a colorless liquid (39°-40° C., 0.1 mm Hg) which was further purified by flash chromatography (silica gel, hexane) to give p-tolyltrimethyltin (7.30 g, 82%) as a colorless liquid;

¹H NMR (300 MHz, CDCl₃) δ7.40 (d, J=7.7 Hz, 2H), 7.19 (d, J=7.7 Hz, 2H), 2.34 (s, 3H), 0.30 (s, 9H).

Step 3: Preparation of 4'-methylbiphenyl-2-tert-butylsulfonamide

2-Bromobenzene(tert-butyl)sulfonamide (1.00 g, 3.92 mmol), p-tolyl-trimethyltin (1.95 g, 6.67 mmol), bis(triphenylphosphine)palladiumII chloride (Aldrich) (165 mg, 0.235 mmol) and dimethylformamide (25 ml) were heated with stirring under nitrogen at 90° C. for 5 hours. The black suspension was cooled to room temperature, then filtered through a pad of celite which was washed with tetrahydrofuran. The colorless filtrate was evaporated to dryness then chromatographed (silica gel, 10% ethyl acetate-hexane) to give 4'-methylbiphenyl-2-tert-butylsulfonamide (0.88 g, 74%) as a white solid; ¹H NMR (300 MHz, CDCl₃) δ8.16 (d, J=7.9 Hz, 1H), 7.60–7.37 (m, 4H), 7.36–7.24 (m, 3H), 3.57 (s, 1H), 2.42 (s, 3H), 0.99 (s, 9H).

Step 4: Preparation of 4'-bromomethylbiphenyl-2-tert-butylsulfonamide

N-Bromosuccinimide (387 mg, 2.17 mmol), α,α'-azoisobutyronitrile (catalytic), 4'-methylbiphenyl-2-tert-butylsulfonamide (550 mg, 1.81 mmol) and carbon tetrachloride (50 ml) were heated with stirring at reflux for 3 hour. After cooling to room temperature the mixture was filtered and the filtrate evaporated to dryness. Flash chromatography (silica gel, initially 10 and then 20% ethyl acetate-hexane) afforded 4'-bromo-methylbiphenyl-2-tert-butylsulfonamide (699 mg, 77% pure (the remainder of the material was 4'-dibromomethyl-biphenyl-2-tert-butylsulfonamide), 97% as a white solid; ¹H NMR (300 MHz, CDCl₃) δ8.17 (dd, J=7.5, 1.6 Hz, 1H), 7.68–7.45 (m, 6H), 7.31 (dd, J=7.5, 1.6 Hz, 1H), 4.55 (s, 2H), 3.52 (s, 1H), 1.00 (s, 9H).

EXAMPLE 2

Preparation of 1-((2'-((tert-butylamino)-sulfonyl)(1,1'-biphenyl)-4-yl)methyl)-2-butyl-4-chloroimidazole-5-carboxylic acid, methyl ester To a stirred solution of 2-butyl-4-chloro-1H-imidazole-5-carboxylic acid, methyl ester (150 mg, 0.692 mmol) in dimethylformamide (10 ml) under nitrogen at room temperature was added potassium carbonate (143 mg, 1.03 mmol). The mixture was heated at 100° C. for 0.5 hours then cooled to room temperature. 4'-Bromomethylbiphenyl-2-tert-butylsulfonamide (393 mg, 74% pure, 0.761 mmol) was added and stirring continued at room temperature for 12 hours. The solvent was removed in vacuo then the residue partitioned between ethyl acetate and water. The organic phase was separated and the aqueous phase re-extracted three times with ethyl acetate. The combined organic phase was washed with brine, dried (magnesium sulfate) and the solvent removed in vacuo. Flash chromatography (silica gel, initially 25 and then 50% ethyl acetate-hexane) afforded two isomers, isomer A: 1-((2'-((tert-butylamino)sulfonyl)(1,1'-biphenyl)-4-yl)methyl)-2-butyl-4-chloro-imidazole-5-carboxylic acid, methyl ester, recrystallised from ethyl acetate-hexane, (197 mg, 55%) as white needles; ¹H NMR (300 MHz, CD₃OD) δ8.10 (d, J=7.7 Hz, 1H), 7.61 (t, J=7.7 Hz, 1H), 7.52 (t, J=7.7 Hz, 1H), 7.45 (d, J=8.1 Hz, 2H), 7.31 (d, J=7.7 Hz, 1H), 7.11 (d, J=8.1 Hz, 2H), 5.70 (s, 2H), 3.82 (s, 3H), 2.74 (t, J=7.4 Hz, 2H), 1.65 (quin, J=7.4 Hz, 2H), 1.35 (m, 2H), 1.00 (s, 9H), 0.92 (t, J=7.4 Hz, 3H); isomer B: 1-((2'-((tert-butylamino)sulfonyl)(1,1'-biphenyl)-4-yl)methyl)-2-butyl-5-chloro-imidazole-4-carboxylic acid, methyl ester (55 mg, 15%) as a white solid; ¹H NMR (300 MHz, CD₃OD) δ8.11 (d, J=7.7 Hz, 1H), 7.60 (t, J=7.7 Hz, 1H), 7.55–7.45 (m, 3H), 7.30 (d, J=7.7 Hz, 1H), 7.15 (d, J=8.1 Hz, 2H), 5.39 (s, 2H), 3.88 (s, 3H), 2.72 (t, J=7.4 Hz, 2H), 1.61 (quin, J=7.4 Hz, 2H), 1.35 (sext, J=7.4 Hz, 2H), 1.01 (s, 9H), 0.90 (t, J=7.4 Hz, 3H).

EXAMPLE 3

Preparation of 1-((2'-(aminosulfonyl)(1,1'-biphenyl)-4-yl)methyl)-2-butyl-4-chloro-imidazole-5-carboxylic acid, methyl ester 1-((2'-((tert-butylamino)sulfonyl)(1,1'-biphenyl)-4yl)-methyl)-2-butyl-4-chloro-imidazole-5-carboxylic acid, methyl ester (75.0 mg, 0.145 mmol) was stirred in trifluoroacetic acid (1.0 ml) containing anisole (20 μl) under nitrogen at room temperature for 24 hours. The trifluoroacetic acid was removed in vacuo and the residue chromatographed (silica gel, 35% ethyl acetate-hexane) to afford 1-((2'-(aminosulfonyl)( 1,1'-biphenyl)-4-yl)methyl)-2-butyl-4-chloro-imidazole-5-carboxylic acid, methyl ester (67.5 mg, 100%) as a white solid; ¹H NMR (300 MHz, CD₃OD/CDCl₃) δ8.08 (d, J=7.7 Hz, 1H), 7.54 (t, J=7.7 Hz, 1H), 7.46 (t, J=7.7 Hz, 1H), 7.40 (d, J=8.1 Hz, 2H), 7.26 (d, J=7.7 Hz, 1H), 7.04 (d, J=8.1 Hz, 2H), 5.57 (s, 2H), 3.80 (s, 3H), 2.64 (t, J=7.4 Hz, 2H), 1.62 (quin, J=7.4 Hz, 2H), 1.31 (sext, J=7.4 Hz, 2H), 0.89 (t, J=7.4 Hz, 3H).

EXAMPLE 4

Preparation of 1-((2'-((benzolylamino)-sulfonyl)(1,1'-biphenyl)-4-yl)methyl)-2-butyl-4-chloroimidazole-5-carboxylic acid, methyl ester To a stirred solution of 1-((2'-aminosulfonyl)(1,1'-biphenyl)-4-yl)methyl)-2-butyl-4-chloro-imidazole-5-carboxylic acid, methyl ester (67.0 mg, 0.145 mmol) in pyridine (1.0 ml) under nitrogen at room temperature was added benzoyl chloride (168 μl, 1.45 mmol) dropwise. The pale orange solution was stirred at room temperature for 12 hours then saturated sodium bicarbonate solution added. The mixture was extracted four times with ethyl acetate. The combined organic phase was washed with water, twice with saturated copper sulfate solution, water, brine and dried (magnesium sulfate). The solvent was removed in vacuo and the residue chromatographed (silica gel, 2% methanol-methylene chloride) to give 1-((2'-((benzoylamino)sulfonyl)(1,1'-biphenyl)-4-yl)methyl)-2-butyl-4-chloro-imidazole-5-carboxylic acid, methyl ester (63.4 mg, 77%) as a white solid; ¹H NMR (300 MHz, CD₃OD) δ8.30 (dd, J=7.7, 1.7 Hz, 1H), 7.65–7.42 (m, 5H), 7.40–7.30 (m, 2H), 7.29–7.18 (m, 3H), 6.90 (d, J=8.2 Hz, 2H), 5.54 (s, 2H), 3.84 (s, 3H), 2.62 (t, J=7.8 Hz, 2H), 1.64 (quin, J=7.8 Hz, 2H), 1.32 (apparent sext, 2H), 0.87 (t, J=7.3 Hz, 3H); FAB-MS: 568 and 566 (M+H).

EXAMPLE 5

Preparation of 1-((2'-((benzoylamino)-sulfonyl)(1,1'-biphenyl)-4-yl)methyl)-2-butyl-4-chloroimidazole-5-carboxylic acid To a stirred suspension of 1-((2'-((benzoylamino)sulfonyl)(1,1'-biphenyl)-4-yl)methyl)-2-butyl-4-chloro-imidazole-5-carboxylic acid, methyl ester (25 mg, 0.044 mmol) in methanol (1.0 ml) was added 2N sodium hydroxide solution (0.50 ml). The pale yellow solution was stirred at room temperature for 3 hours then the methanol was removed in vacuo. Saturated sodium dihydrogen phosphate solution was added followed by ethyl acetate and the organic phase separated. The aqueous phase was re-extracted twice with ethyl acetate, then the combined organic phase washed with brine, dried (magnesium sulfate) and the solvent removed in vacuo. Flash chromatography (silica gel, 0.25% acetic acid-2.5% methanolmethylene chloride) afforded 1-((2'-((benzoylamino)sulfonyl)(1,1'-biphenyl)-4-yl)methyl)2-butyl-4-chloro-imidazole-5-carboxylic acid (11.5 mg, 47%) as a white solid; $^1$H NMR (300 MHz, CD$_3$OD) δ8.27 (d, J=8.5 Hz, 1H), 7.71-7.50 (m, 3H), 7.50-7.36 (m, 4H), 7.35-7.23 (m, 3H), 6.98 (d, J=8.0 Hz, 2H), 5.70 (s, 2H), 2.67 (apparent t, 2H), 1.64 (apparent quin, 2H), 1.35 (apparent sext, 2H), 0.90 (t, J=7.3 Hz, 3H); FAB-MS: 574 (M+Na), 552 (M+H).

EXAMPLE 6

2-Butyl-4-chloro-5-formylimidazole

To a solution of 2-butyl-4-chloro-5-hydroxyimdazole (5.0 g, 26,5 mMol) in methanol (300 ml) were added MnO$_2$ (57.6 g, 0.663 mol) and 3A° powdered molecular sieves (oven dried in vacuo) (4.5 g), and the mixture was stirred at room temperature for 20 h. The reaction was filtered through a pad of celite. The filtrate was evaporated in vacuo to give the pure desired aldehyde (purity checked on TlC using EtOAc-Hexane 1:3) in quantitative yield (4.9 g, white solid). This material was used directly in the subsequent steps as described below.

$^1$H-NMR (CDCl$_3$): δ0.94 (t, J=7.5 Hz, 3H), 1.35 (m, 2H), 1.68 (m, 2H), 2.7 (t, J=7.5 Hz, 2H), 4.9 (broad s, 1H), 9.64 (s, IH).

EXAMPLE 7

2-Butyl-5-carbomethoxy-4-chloroimidazole

To a solution of 2-Butyl-4-chloro-5-formylimidazole (4.9 g, 26 mMol) in methanol (350 ml) were added NaCN (12.98 g, 0.26 Mol), glacial AcOH (2.5 ml) and MnO$_2$ (57.6 g, 0.663 Mol), and the mixture was stirred at room temperature for 72 h. The reaction was filtered through a pad of celite and concentrated in vacuo. The residue obtained was partitioned between EtOAc (150 ml) and water (50 ml), and the organic phase was washed with brine and then dried over sodium sulfate. The crude product (5.73 g), obtained after removal of the solvent under reduced pressure, was purified by flash-chromatography on silica-gel using EtOAc-hexane (1:5). Yield 4.5 g (80%, white solid). The product was crystallized from ethylacetate-hexane to give fine needles.

$^1$H-NMR (CDCl$_3$): δ0.91 (t, J=7.5 Hz, 3H), 1.35 (m, 2H), 1.72 (m, 2H), 2.73 (t, J=7.5 Hz, 2H), 3.9 (s, 3H). FAB-MS: m/e 217,219 (M+H).

EXAMPLE 8

Preparation of 2-t-Butoxycarbonyl-4'-bromomethylbiphenyl

Step 1: 2-t-Butoxycarbonyl-4'-methylbiphenyl

To a solution of p-bromotoluene (30 g) in dry ether (150 ml) at −78° C., a solution of t-BuLi in pentane (1.7M) (210 ml) was added slowly over a period of 1 hour and 30 minutes, using a dropping funnel. The bath was then removed and the mixture was stirred at room temperature for an additional 2 hours. The content of the flask was then added slowly (using a cannula) at room temperature to a premixed solution of ZnCl$_2$ in ether (1M) (180 ml) and dry THF (360 ml). The mixture was stirred for 2 hours at that temperature and the slurry was added (using a cannula) to a solution of 2-t-butoxycarbonyliodobenzene (35.6 g), and NiCl$_2$(Ph$_3$P)$_2$ (2.1 g) in dry THF (360 ml). The mixture, after stirring at room temperature overnight (18 hours), was poured slowly under stirring into ice-cold 0.5N HCl (1500 ml). The organic layer was separated, and the aqueous phase was extracted with ether (3×300 ml). The combined organic layer was washed with water, brine and then dried over MgSO$_4$. Removal of the solvent gave the crude product as an oil (32 g). The material was purified on a silica gel flash column using ethylacetate/hexane (1:12) to give the titled compound as an oil (24 g, 76%). NMR (CDCl$_3$) δ1.24 (s, 9H), 2.42 (s, 3H), 7.2-7.8 (m, 8H); FAB-MS: m/e 269 (M+H).

Step 2: 2-t-Butoxycarbonyl-4'-bromomethylbiphenyl

The titled compound was prepared from 2-t-Butoxycarbonyl-4'-methylbiphenyl (obtained from Step 1) according to the procedure described in European Patent Application EP 0,253,310.

EXAMPLE 9

Preparation of N-Triphenylmethyl-5-(4'-bromomethylbiphen-2-yl)tetrazole

Step 1: 2-cyano-4'-methylbiphenyl

To a solution of p-bromotoluene (30 g) in dry ether (150 ml) at −78° C., a solution of t-BuLi in pentane (1.7M) (210 ml) was added slowly over a period of 1 hour and 30 minutes, using a dropping funnel. The bath was then removed and the mixture was stirred at room temperature for an additional 2 hours. The content of the flask was then added slowly (using a cannula) at room temperature to a premixed solution of ZnCl$_2$ in ether (1M) (180 ml) and dry THF (360 mL). The mixture was stirred for 2 hours at that temperature and the slurry was added (using a cannula) to a solution of 2-bromobenzonitrile (21.3 g) and NiCl$_2$(Ph$_3$P)$_2$ (2.1 g) in dry THF (300 ml). The mixture, after stirring at room temperature overnight (18 hours), was poured slowly under stirring into ice cold 0.5N HCl (1500 ml). The organic layer was separated, and the aqueous phase was extracted with ether (3×300 ml). The combined organic layer was washer with water, brine and then dried over MgSO$_4$. Removal of the solvent gave the crude product as a semisolid mass (34 g). The material was purified on a silica gel flash column using ethylacetate/hexane (1:12) to give the desired nitrile as a low melting solid (28 g, 88%). NMR (CDCl$_3$) δ2.42 (s, 3H), 7.2-7.8 (m, 8H); FAB-MS: m/e 194 (M+H).

Step 2: Trimethylstannyl azide

To a concentrated solution of NaN$_3$ (40 g) in water (100 ml), a solution of trimethyltin chloride (20 g) in dioxane (10 ml) was added in three portions under vigorous stirring. An instantaneous precipitate formation was observed. The mixture, after stirring overnight at room temperature, was filtered. The residue was washed with water, and dried under suction and the in vacuo over P$_2$O$_5$. Yield 18.7 g (81%), mp 132°-136° C.

Step 3: N-Triphenylmethyl-5-(4'-bromomethylbiphen-2-yl)tetrazole

The titled compound was prepared starting from 2-cyano-4'-methylbiphenyl (Step 1) as described in European Patent Application EP 0,291,969.

EXAMPLE 10

Step 1: 4-Methyl-2'-nitrobiphenyl

A 1 L three-necked 24/40 round-bottom flask equipped with a mechanical stirrer, a 250 mL constant pressure addition funnel with a nitrogen inlet at the top, and a septum was flame dried, cooled and then charged with a solution of 29.07 f (0.17 mol) of p-bromotoluene in 100 mL of anhydrous tetrahydrofuran under a nitrogen atmosphere. The solution was stirred and cooled to $-78°$ C. and 200 mL (0.34 mol) of a 1.7M solution of t-butyllithium in pentane was added via the addition funnel over 30 minutes. When the addition was complete, the cooling bath was removed and the reaction mixture was stirred for 30 minutes and allowed to warm to room temperature. The dropping funnel was next charged with 170 mL (0.17 mol) of a 1.0M solution of zinc chloride in diethylether which was added to the reaction mixture over a 10 minute period. A separate 1 L three-necked 24/40 round-bottom flask equipped with a mechanical stirrer, a nitrogen inlet and a septum, was flame dried, cooled and then charged with 4.04 g (6.0 mmol) of bis(triphenylphosphine)palladium(II) chloride and 50 mL of anhydrous tetrahydrofuran under a nitrogen atmosphere. The stirrer was started and 8.0 mL of a 1.5M solution (12 mmol) of diisobutylaluminum hydride in toluene was added to the suspension via syringe. The catalyst was stirred an additional 10 minutes at room temperature, and then a solution of 23.23 g (0.115 mol) of 1-bromo-2-nitrobenzene in 100 mL of anhydrous tetrahydrofuran was added. The suspension of the tolylzinc chloride was then transferred to the second flask via a wide diameter cannula. The reaction mixture was stirred an additional 45 minutes at room temperature, then most of the tetrahydrofuran was removed on a rotary evaporator. The resulting oil was partitioned between ethyl acetate and 1.0N hydrochloric acid. The organic layer was washed successively with water and brine, then dried (MgSO$_4$), filtered and evaporated. The residual oil was purified on a silica gel flash chromatography column eluted with 10% ethyl acetate-hexane to afford after evaporation and drying in vacuo 15.43 g (63%) of the product as a viscous yellow oil: NMR (CDCl$_3$): δ2.36 (s, 3H), 7.16–7.24 (m, 4H), 7.38–7.46 (m, 2H), 7.55–7.62 (m, 1H), 7.80 (d, J=10 Hz, 1H); MS (FAB) m/e 214 (MH+).

Step 2: 4-Bromomethyl-2'-nitrobiphenyl

A 2 L 24/40 three necked round-bottom flask equipped with a mechanical stirrer, a reflux condenser and a stopper, was charged with 15.427 g (72 mmol) of 4-methyl-2'-nitro[1,1'-biphenyl], 1.2 L of carbon tetrachloride, 14.164 g (80 mmol) of N-bromosuccinimide, and 0.50 g of 2,2'-azobis-(2-methylpropionitrile). The stirred reaction mixture was refluxed under a nitrogen atmosphere for 4 hours, then cooled to room temperature and filtered. The filtrate was evaporated in vacuo and the residual oil was purified on a silica gel flash chromatography column eluted with 10% ethyl acetate-hexane. Evaporation of the pure fractions afforded the product as a yellow crystalline solid (7.83 g, 37%) which had: mp 109°-110° C.; NMR (CDCl$_3$): δ4.52 (s, 2H), 7.24–7.30 (m, 2H), 7.40–7.52 (m, 4H), 7.58–7.65 (m, 1H), 7.86 (d, J=10 Hz, 1H); MS (FAB) m/e 294 (MH+).

EXAMPLE 11

2-Butyl-5-carbomethoxy-4-chloro-1-[(2'-t-butoxycarbonyl)biphen-4-yl)methyl]imidazole To a solution of 2-Butyl-5-carbomethoxy-4-chloroimidazole (0.5 g, 2.3 mMol) in anhydrous DMF (15 ml) was added anhydrous K$_2$CO$_3$ (0.48 g, 3.5 mMol) and stirred at 50° C. for 30 min. After cooling down to room temperature, 2-t-butoxycarbonyl-4'-bromomethyl biphenyl (0.854 g, 2.46 mMol) was added to the reaction and stirred at room temperature for 18 h under N$_2$. The solvent was removed in vacuo, and the residue was treated with water (20 ml) and extracted with ethylacetate (3×30 ml). The combined organic phase was washed with brine and then dried over anhydrous Na$_2$SO$_4$. Removal of the solvent gave the crude material as a foam, which was then purified by flash-chromatography on silica-gel using EtOAc-Hexane (1:5). The desired product (less polar isomer) was obtained as a foam after removal of the solvent in vacuo. Yield 0.85 g (53%).

$^1$H-NMR (CDCl$_3$): δ0.854 (t, J=7.5 Hz, 3H), 1.21 (s, 9H), 1.29 (m, 2H), 1.64 (m, 2H), 2.51 (t, J=7.5 Hz, 2H), 3.75 (s, 3H), 5.45 (s, 2H ), 6.76 (d, J=8Hz, 2H), 6.94 (m, 5H), 7.09 (d, J=8 Hz, 2H), 7.9 (m, 1H).

EXAMPLE 12

2-Butyl-4-chloro-1-[(2'-t-butoxycarbonyl)biphen-4-yl)methyl]-imidazole-5-carboxylic acid To a solution of 2-Butyl-5-carbomethoxy-4-chloro-1-[(2'-t-butoxycarbonyl)-biphen-4-yl)-methyl]imidazole (0.278 g, 0.577 mMol) in methanol (10 ml) was added 2N NaOH (8 ml), and the mixture was stirred at room temperature for 4 h. The reaction mixture was aciodified with saturated NaH$_2$PO$_4$ (pH∼5.0) and concentrated in vacuo. The residue was dissolved in water (5 ml) and extracted with chloroform (3×30 ml). The combined organic phase was washed with brine and then dried over Na$_2$SO$_4$. Removal of the solvent in vacuo gave the crude product, which was purified by flash chromatography using chloroform-methanol-acetic acid (100:6:1) to give the pure desired product as a glass like solid (0.21 g). The glass like solid was triturared with ether-hexane (1:1) (3 ml) and filtered to give a white powder (0.195 g, 78%).

$^1$H-NMR (CDCl$_3$): δ0.82 (t, J=7.5 Hz, 3H), 1.19 (s, 9H), 1.29 (m, 2H), 1.62 (m, 2H), 2.61 (t, J=7.5 Hz, 2H), 5.45 (s, 2H), 6.87 (d, J=8 Hz, 2H), 7.08 (d, J=8 Hz, 2H), 7.3–7.6 (m, 3H), 7.98 (d, J=7.5 Hz, 1H). FAB-MS: m/e 467,469 (M+H).

EXAMPLE 13

2-Butyl-5-(N-(phenylsulfonyl)-carboxamido)-4-chloro-1-[(2'-t-butoxycarbonyl-biphen-4-yl)methyl]imidazole To a solution of 2-Butyl-4-chloro-1-[(2'-t-butoxycarbonyl)biphen-4-yl)methyl]imidazole-5-carboxylic acid (0.11 g, 0.235 mMol) in dry THF (3 ml) was added 1,1'-carbonyldiimidazole (0.046 g, 0.282 mMol), and the mixture was refluxed for 2 h. To this mixture, after cooling to room temperature, was added a solution of benzenesulfonamide (0.55 g, 0.353 mMol) and DBU (0.05 ml, 0.353 mMol). The resulting mixture was stirred at 50° C. for 4 h and then concentrated in vacuo. The residue, thus obtained, was dissolved in water (5 ml) and acidified with 10% aqueous NaH$_2$PO$_4$ to pH 5.0. The resulting mixture was then extracted with chloroform (3×20 ml), and the combined organic phase was washed with brine and then dried over MgSO$_4$. Removal of the solvent in vacuo gave the crude product which was then purified by flash-chromatography on silica-gel using chloroform: methanol: ammonium hydroxide (70:10:1) to give the titled product as a foam (0.096 g). $^1$H-NMR (CDCl$_3$): δ0.82 (t, J=7.5 Hz, 3H), 1.19 (s, 9H), 1.29 (m, 2H), 1.62 (m, 2H), 2.61 (t, J=7.5 Hz, 2H), 5.52 (s, 2H), 6.87 (d, J=8 Hz, 2H), 7.15 (d, J=8 Hz, 2H), 7.2–7.9 (m, 8H), 8.1 (d, J=7.5 Hz, 1H). FAB-MS: m/e 607,609 (M+H).

EXAMPLE 14

2-Butyl-5-(N-(phenylsulfonyl)-carboxamido)-4-chloro-1-[(2'-carboxy-biphen-4-yl)methyl]imidazole To a solution of 2-Butyl-5-(N-(phenylsulfonyl)carboxamido)-4-chloro-1-[(2'-t-butoxycarbonyl-biphen-4-yl)methyl]imidazole (0.047 g) in methylene chloride (0.5 ml) was added anisole (0.02 ml) and trifluoroacetic acid (0.5 ml), and the mixture was stirred for 5 h at room temperature. The residue, obtained after removal of the solvent in vacuo, was triturated with ether to give white solid which was filtered and dried in vacuo overnight. Yield 0.035 g.

$^1$H-NMR (CD$_3$OD): δ0.82 (t, J=7.5 Hz, 3H), 1.33 (m, 2H), 1.62 (m, 2H), 2.71 (t, J=7.5 Hz, 2H), 5.35 (s, 2H), 6.87 (d, J=8 Hz, 2H), 7.12 (d, J=8 Hz, 2H), 7.2–7.9 (m, 8H), 8.1 (d, J=7.5 Hz, 1H). FAB-MS: m/e 551,553 (M+H).

EXAMPLE 15

Typical Pharmaceutical Compositions Containing a Compound of the Invention

A: Dry Filled Capsules Containing 50 mg of Active Ingredient Per Capsule

| Ingredient | Amount per capsule (mg) |
|---|---|
| 2-Butyl-5-(N-(phenylsulfonyl)-carboxamido)-4-chloro-1-[(2'-carboxy-biphen-4-yl)methyl]-imidazole | 50 |
| Lactose | 149 |
| Magnesium stearate | 1 |
| Capsule (size No. 1) | 200 |

The 2-Butyl-5-(N-(phenylsulfonyl)-carboxamido)-4-chloro-1-[(2'-carboxy-biphen-4-yl)methyl]imidazole can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 2-Butyl-5-(N-(phenylsulfonyl)-carboxamido)-4-chloro-1-[(2'-carboxy-biphen-4-yl)methyl]imidazole 1(25 mg), pregelatinized starch USP (82 mg), microcrystalline cellulose (82 mg) and magnesium stearate (1 mg).

C: Combination Tablet

A typical combination tablet would contain, for example, a diuretic such as hydrochlorothiazide and consist of 2-Butyl-5-(N-(phenylsulfonyl)-carboxamido)-4-chloro-1-[(2'-carboxy-biphen-4-yl)methyl]imidazole (50 mg) pregelatinized starch USP (82 mg), microcrystalline cellulose (82 mg) and magnesium stearate (1 mg).

D: Suppository

Typical suppository formulations for rectal administration can contain 2-Butyl-5-(phenylsulfonyl)-carboxamido)-4-chloro-1-[(2'-carboxy-biphen-4-yl)-methyl]imidazole (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme inhibitor and/or a calcium channel blocker in pharmaceutically effective amounts as described, for example, in C above.

E: Injection

A typical injectible formulation would contain 2-Butyl-5-(N-(phenylsulfonyl)-carboxamido)-4-chloro-1-[(2'-carboxy-biphen-4-yl)-methyl]-imidazole sodium phosphate dibasic anhydrous (11.4 mg) benzyl alcohol (0.01 ml) and water for injection (1.0 ml). Such an injectible formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of structural formula I

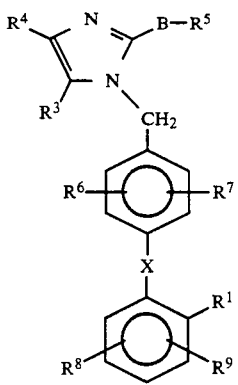

or a pharmaceutically acceptable salt thereof wherein:
R$^1$ is
  (a) —CO$_2$R$^{10}$,
  (b) —NHSO$_2$R$^{12}$,
  (c) —SO$_2$NHR$^{12}$,

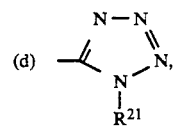

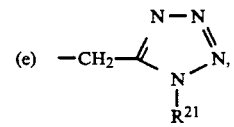

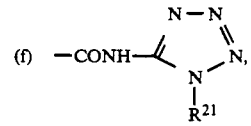

(g) —CONHNHSO$_2$CF$_3$,
  (h) —CH$_2$SO$_2$NHR$^{12}$,
  (i) —SO$_2$NHCOR$^{12}$,
  (j) —CH$_2$SO$_2$NHCOR$^{12}$,
  (k) —CONHSO$_2$R$^{12}$, (l) —CH$_2$CONHSO$_2$R$^{12}$,
(m) —NHSO$_2$NHCOR$^{12}$,
(n) —NHCONHSO$_2$R$^{12}$,
(o) —SO$_2$NHCONR$^{2a}$R$^{12}$, or
(p) —CONHSO$_2$NR$^{2a}$R$^{12}$;

R$^2$ is:
(a) H, or
(b) (C$_1$-C$_6$)-alkyl;

R$^{2a}$ is:
(a) R$^2$,
(b) —CH$_2$-aryl, wherein aryl is phenyl or naphthyl unsubstituted or substituted with 1 or 2 substituents selected from the group consisting of:
  i) Cl, Br, I, F,
  ii) (C$_1$-C$_4$)-alkyl,
  iii) (C$_1$-C$_4$)-alkoxy,
  iv) NO$_2$,
  v) CF$_3$,
  vi) (C$_1$-C$_4$)-alkylthio,
  vii) hydroxy,
  viii) amino,
  ix) (C$_3$-C$_7$)-cycloalkyl,
  x) (C$_3$-C$_{10}$)-alkenyl, or
  xi) CN, or
(c) aryl as defined in R$^{2a}$(b) above;

R$^3$ is:
(a) —SO$_2$NHR$^{12}$,
(b) —CH$_2$SO$_2$NHR$^{12}$,
(c) —SO$_2$NHCOR$^{12}$,
(d) —CH$_2$SO$_2$NHCOR$^{12}$,
(e) —CONHSO$_2$R$^{12}$,
(f) —CH$_2$CONHSO$_2$R$^{12}$,
(g) —NHSO$_2$NHCOR$^{12}$,
(h) —NHCONHSO$_2$R$^{12}$,
(i) —SO$_2$NHCONR$^{2a}$R$^{12}$,
(j) —CONHSO$_2$NR$^{2a}$R$^{12}$, or
(k) —NHSO$_2$R$^{12}$;

y is 0 or 1;

R$^4$ is:
(a) H,
(b) (C$_1$-C$_8$)-alkyl, (C$_2$-C$_6$)-alkenyl or (C$_2$-C$_6$)-alkynyl,
(c) Cl, Br, I, F,
(d) NO$_2$,
(e) (C$_1$-C$_8$)-perfluoroalkyl,
(f) (C$_1$-C$_8$)-perfluoroalkenyl,
(g) pentafluorophenyl,
(h) CN,
(i) phenyl,
(j) phenyl-(C$_1$-C$_3$)-alkyl,
(k) phenyl and phenyl-(C$_1$-C$_3$)-alkyl substituted on the phenyl ring with one or two substituents selected from:
  i) (C$_1$-C$_4$)-alkyl,
  ii) (C$_1$-C$_4$)-alkoxy,
  iii) F, Cl, Br, I,
  iv) hydroxy,
  v) CF$_3$,
  vi) CO$_2$R$^{2a}$,
  vii) NO$_2$, or
  viii) SO$_2$NR$^{2a}$R$^{2a}$;
(l) phenyl-(C$_2$-C$_6$)-alkenyl, (m) 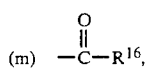

(n) —(CH$_2$)$_n$—S(O)$_x$R$^{15}$, (o) 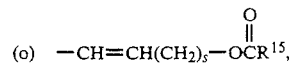

(p) 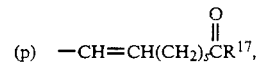

(q) 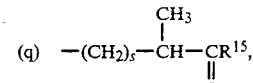

(r) 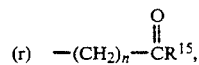

(s) 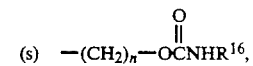

(t) 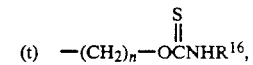

(u) —(CH$_2$)$_n$—NHSO$_2$R$^{16}$, or
(v) —(CH$_2$)$_n$—F;

R$^5$ is:
(a) (C$_1$-C$_9$)-alkyl, (C$_2$-C$_6$)-alkenyl or (C$_2$-C$_6$)-alkynyl each of which is unsubstituted or substituted with a substituent selected from the group consisting of:
  i) aryl as defined in R$^{2a}$(b) above,
  ii) (C$_3$-C$_7$)-cycloalkyl,
  iii) Cl, Br, I, F,
  iv) COOR$^2$,
  vii) N((C$_1$-C$_4$)-alkyl)$_2$,
  viii) NHSO$_2$R$^2$,
  ix) CF$_3$,
  x) COOR$^2$, or
  xi) SO$_2$NHR$^{2a}$,
(b) aryl, or
(d) (C$_1$-C$_4$)-perfluoroalkyl;

B is a single bond;
x is 0 to 2;
s is 0 to 5;
m is 1 to 5;
p is 0 to 3;
n is 1 to 10;

R$^6$ is:
(a) H,
(b) Cl, Br, I, F,
(c) (C$_1$-C$_6$)-alkyl,
(d) (C$_1$-C$_6$)-alkoxy, or
(e) (C$_1$-C$_6$)-alkoxyalkyl;

R$^7$ is:
(a) H,
(b) Cl, Br, I, F,
(c) NO$_2$,
(d) (C$_1$-C$_6$)-alkyl,
(e) (C$_1$-C$_6$)-acyloxy,
(f) (C$_3$-C$_6$)-cycloalkyl,
(g) (C$_1$-C$_6$)-alkoxy,
(h) —NHSO$_2$R$^{2a}$,
(i) hydroxy (C$_1$-C$_4$)-alkyl,
(j) (C$_1$-C$_4$)-alkyl-aryl,
(k) aryl-(C$_1$-C$_4$)-alkyl,
(l) (C$_1$-C$_4$)-alkylthio,
(m) (C$_1$-C$_4$)-alkylsulfinyl,
(n) (C$_1$-C$_4$)-alkylsulfonyl,
(o) NH$_2$, (p) NH(($C_1$-$C_4$)-alkyl),
(q) N(($C_1$-$C_4$)-alkyl)$_2$,
(r) ($C_1$-$C_4$)-fluoroalkyl,
(s) —$SO_2$—$NHR^{10}$,
(t) aryl,
(u) furyl, or
(v) —$COOR^{11}$;

$R^8$ and $R^9$ are independently:
H, Cl, Br, I, F, —$NO_2$, —$NH_2$, NH(($C_1$-$C_4$)-alkyl), N(($C_1$-$C_4$) alkyl)$_2$, —$SO_2NHR^{10}$, $CF_3$, ($C_1$-$C_6$)-alkyl, ($C_1$-$C_6$)-alkoxy, ($C_2$-$C_6$)-alkenyl, ($C_2$-$C_6$)-alkynyl or when $R^8$ and $R^9$ are on adjacent carbon atoms, they are joined to form an aryl ring;

$R^{10}$ is: H, ($C_1$-$C_5$)-alkyl, aryl or —$CH_2$-aryl, wherein aryl is as defined in $R^{2a}$(b);

$R^{11}$ is

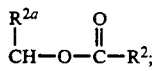

$R^{12}$ is:
(a) aryl as defined in $R^{2a}$(b),
(b) heteroaryl, wherein heteroaryl is defined as an unsubstituted, monosubstituted or disubstituted hetero aromatic ring selected from the group consisting of: isoxazolyl, and pyrimidyl, wherein the substituents are members selected from the group consisting of: —OH, —SH, —($C_1$-$C_4$)-alkyl, —($C_1$-$C_4$)-alkoxy, —$CF_3$, Cl, Br, F, I, —$NO_2$, —$CO_2$H, —$CO_2$—($C_1$-$C_4$)-alkyl, —$NH_2$, —NH(($C_1$-$C_4$)-alkyl), or —N(($C_1$-$C_4$)-alkyl)$_2$,
(c) ($C_3$-$C_4$)-cycloalkyl,
(d) ($C_1$-$C_4$)-alkyl which is unsubstituted or substituted with a substituent selected from the group consisting of: aryl as defined in $R^{2a}$(b), heteroaryl as defined above in $R^{12}$(b), —OH, —SH, ($C_1$-$C_4$)-alkyl, —O—($C_1$-$C_4$)-alkyl —S(O)$_x$—($C_1$-$C_4$)-alkyl, —$CF_3$, Cl, Br, F, I, —$NO_2$, —$CO_2$H, —$CO_2$—($C_1$-$C_4$)-alkyl, —$NH_2$, —NH[($C_1$-$C_4$)-alkyl], —$NHCOR^{2a}$, or —N[($C_1$-$C_4$)-alkyl]$_2$, or
(e) ($C_1$-$C_4$)-perfluoroalkyl;

$R^{13}$ is:
(a) H,
(b) ($C_1$-$C_6$)-alkyl,
(c) aryl as defined in $R^{2a}$(b),
(d) aryl-($C_1$-$C_6$)-alkyl-(C=O)—, wherein aryl is as defined in $R^{2a}$(b),
(e) ($C_1$-$C_6$)-alkyl-(C=O)—,
(f) ($C_3$-$C_6$)-cycloalkyl, or
(g) allyl;

$R^{14}$ is:
(a) H,
(b) ($C_1$-$C_8$)-alkyl,
(c) phenyl, or
(d) benzyl;

$R^{15}$ is:

(a) H,
(b) ($C_1$-$C_6$)-alkyl,
(c) ($C_3$-$C_6$)-cycloalkyl,
(d) —($CH_2$)$_p$-phenyl,
(e) —$OR^{17}$,
(f) morpholin-4-yl, or
(g) —$NR^{18}R^{19}$;

$R^{16}$ is:
(a) ($C_1$-$C_8$)-alkyl,
(b) ($C_1$-$C_8$)-perfluoroalkyl,
(c) 1-adamantyl,
(d) 1-naphthyl,
(e) (1-naphthyl)ethyl, or
(f) —($CH_2$)$_p$-phenyl;

$R^{17}$ is:
(a) H,
(b) ($C_1$-$C_6$)-alkyl,
(c) ($C_3$-$C_6$)-cycloalkyl,
(d) phenyl, or
(e) benzyl;

$R^{18}$ and $R^{19}$ are independently:
(a) H,
(b) ($C_1$-$C_4$)-alkyl,
(c) phenyl,
(d) benzyl, or
(e) α-methylbenzyl;

$R^{20}$ is:
(a) H,
(b) ($C_1$-$C_6$)-alkyl,
(c) ($C_3$-$C_6$)-cycloalkyl, or
(d) —$CH_2$-aryl;

$R^{21}$ is:
(a) H,
(b) ($C_1$-$C_6$)-alkyl,
(c) ($C_2$-$C_4$)-alkenyl, or
(d) ($C_1$-$C_4$)-alkoxy-($C_1$-$C_4$)-alkyl;

$R^{22}$ is:
(a) CN,
(b) $NO_2$, or
(c) $COOR^{10}$; and

X is a carbon-carbon single bond.

2. A compound of structural formula

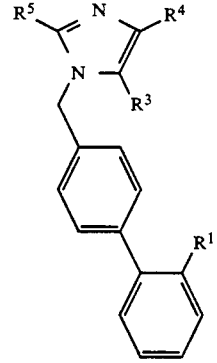

or its pharmaceutically acceptable salt, wherein the compound is selected from the group consisting of:

| R$^1$ | R$^3$ | R$^4$ | R$^5$ |
|---|---|---|---|
| —SO$_2$NHCOPh | —CONHSO$_2$Ph | Cl | n-butyl |

-continued

| R¹ | R³ | R⁴ | R⁵ |
|---|---|---|---|
| —SO₂NHCO—△ | —CONHSO₂Ph | Cl | n-butyl |
| —SO₂NHCO(CH₂)₅NH₂ | —CONHSO₂Ph | Cl | n-butyl |
| —SO₂NHCO(CH₂)₄COOEt | —CONHSO₂Ph | Cl | n-butyl |
| —SO₂NHCO(CH₂)₂-cyclopentyl | —CONHSO₂Ph | Cl | n-butyl |
| —SO₂NHCO-C₆H₄-4-F | —CONHSO₂Ph | Cl | n-butyl |
| —SO₂NHCO-C₆H₄-4-N(CH₃)₂ | —CONHSO₂Ph | Cl | n-butyl |
| —NHSO₂NHCOPh | —CONHSO₂Ph | Cl | n-butyl |
| —SO₂NHCON(CH₃)(Ph) | —CONHSO₂Ph | Cl | n-butyl |
| —SO₂NH-(4,6-dimethylpyrimidin-2-yl) | —CONHSO₂Ph | Cl | n-butyl |
| —SO₂NHCO(CH₂)₂-cyclopentyl | —CONHSO₂Ph | Cl | n-butyl |
| —SO₂NHCO-C₆H₄-4-F | —CONHSO₂Ph | Cl | n-butyl |
| —SO₂NHCO-C₆H₄-4-N(CH₃)₂ | —CONHSO₂Ph | Cl | n-butyl |
| —NHSO₂NHCOPh | —CONHSO₂Ph | Cl | n-butyl |
| —SO₂NHCON(CH₃)(Ph) | —CONHSO₂Ph | Cl | n-butyl |
| —SO₂NH-(4,6-dimethylpyrimidin-2-yl) | —CONHSO₂Ph | Cl | n-butyl |

-continued

| R$^1$ | R$^3$ | R$^4$ | R$^5$ |
|---|---|---|---|
| 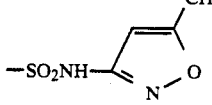 | —CONHSO$_2$Ph | Cl | n-butyl |
| —COOH | —CONHSO$_2$Ph | Cl | n-butyl |
| tetrazol-5-yl | —CONHSO$_2$Ph | Cl | n-butyl |
| tetrazol-5-yl | —SO$_2$NHCOPh | Cl | n-butyl |
| tetrazol-5-yl | 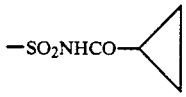 | Cl | n-propyl |
| 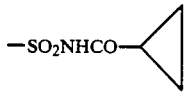 | —SO$_2$NHCOPh | ethyl | n-propyl |
| tetrazol-5-yl | 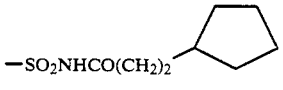 | ethyl | n-propyl |
| tetrazol-5-yl | 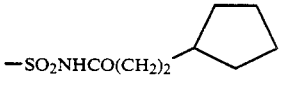 | ethyl | n-propyl |
| —SO$_2$NHCOPh | 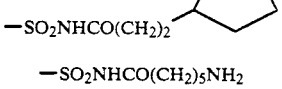 | ethyl | n-propyl |
| 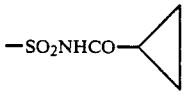 | —SO$_2$NHCO(CH$_2$)$_5$NH$_2$ | ethyl | n-propyl |
| 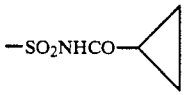 | —SO$_2$NHCO(CH$_2$)$_5$NH$_2$ | H | n-propyl |
| —SO$_2$NHCOPh | —SO$_2$NHCO(CH$_2$)$_5$NH$_2$ | H | n-butyl |
| —SO$_2$NHCOPh | —CONHSO$_2$Ph | ethyl | n-propyl |
| —SO$_2$NHCO(CH$_2$)$_5$NH$_2$ | —COOCH$_2$OC(O)CH$_3$ | ethyl | n-propyl |
| tetrazol-5-yl | 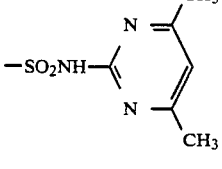 | Cl | n-butyl |
| tetrazol-5-yl | 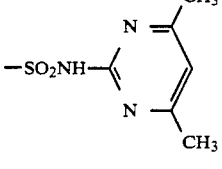 | H | n-butyl |
| tetrazol-5-yl | 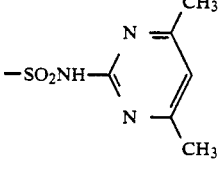 | Cl | n-propyl |

-continued

| R¹ | R³ | R⁴ | R⁵ |
|---|---|---|---|
| —SO₂NHCOPh | 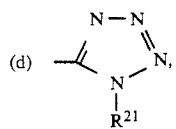 | Cl | n-propyl |
| —NHSO₂NHCOPh | —CONHSO₂Ph | Cl | n-propyl |
| —NHSO₂NHCOPh | —CONHSO₂Ph | ethyl | n-propyl |
| —SO₂NHCOPh | —SO₂NHCOPh | CF₂CF₃ | n-propyl |

3. A pharmaceutical composition useful in the treatment of hypertension which comprises a pharmaceutically acceptable carrier and a pharmaceutically effective amount of a compound of claim 1.

4. A method of treating hypertension which comprises administering to a patient in need of such treatment a pharmaceutically effective amount of a compound of claim 1.

5. An ophthalmological formulation for the treatment of ocular hypertension comprising an ophthalmologically acceptable carrier and an effective ocular antihypertensive amount of a compound of claim 1.

6. A method of treating ocular hypertension comprising administering to a patient in need of such treatment an effective ocular antihypertensive amount of a compound of claim 1.

7. A method of treating cognitive dysfunction, anxiety, or depression comprising administering to a patient in need of such treatment, a therapeutically effective amount of a compound of claim 1.

8. A compound of claim 1 or a pharmaceutically acceptable salt wherein:

$R^1$ is
  (a) —CO₂R¹⁰,
  (b) —NHSO₂R¹²,
  (c) —SO₂NHR¹², (d) 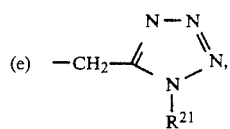

(e) —CH₂— 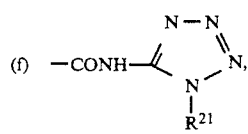

(f) —CONH— (tetrazole with R²¹), (g) —CONHNHSO₂CF₃,
  (h) —CH₂SO₂NHR¹²,
  (i) —SO₂NHCOR¹²,
  (j) —CH₂SO₂NHCOR¹²,
  (k) —CONHSO₂R¹²,
  (l) —CH₂CONHSO₂R¹²,
  (m) —NHSO₂NHCOR¹²,
  (n) —NHCONHSO₂R¹²,
  (o) —SO₂NHCONR²ᵃR¹², or
  (p) —CONHSO₂NR²ᵃR¹²;

$R^3$ is:
  (a) —SO₂NHR¹²,
  (b) —CH₂SO₂NHR¹²,
  (c) —SO₂NHCOR¹²,
  (d) —CH₂SO₂NHCOR¹²,
  (e) —CONHSO₂R¹²,
  (f) —CH₂CONHSO₂R¹²,
  (g) —NHSO₂NHCOR¹², or
  (h) —NHCONHSO₂R¹²;

B is: a single bond;

$R^4$ is:
  (a) H,
  (b) (C₁–C₈)-alkyl, (C₂–C₆)-alkenyl or (C₂–C₆)-alkynyl,
  (c) Cl, Br, I, F,
  (d) NO₂,
  (e) (C₁–C₈)-perfluoroalkyl,
  (f) (C₁–C₈)-perfluoroalkenyl,
  (g) pentafluorophenyl,
  (h) CN,
  (i) phenyl,
  (j) phenyl-(C₁–C₃)-alkyl,
  (k) phenyl and phenyl-(C₁–C₃)-alkyl substituted on the phenyl ring with one or two substituents selected from the group consisting of:
   i) (C₁–C₄)-alkyl,
   ii) (C₁–C₄)-alkoxy,
   iii) F, Cl, Br, I,
   iv) hydroxy,
   v) CF₃,
   vi) CO₂R²ᵃ,
   vii) NO₂, and
   viii) SO₂NR²ᵃR²ᵃ;
  (l) phenyl-(C₂–C₆)-alkenyl, (m) 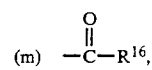

(n) —(CH₂)ₙ—SO₂R¹⁵, wherein n is 0–4, (o) 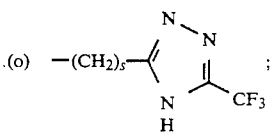

$R^5$ is:
  (a) (C₁–C₉)-alkyl, (C₂–C₆)-alkenyl or (C₂–C₆)-alkynyl each of which is unsubstituted or substituted with a substituent selected from the group consisting of:
i) aryl as defined in $R^{2a}$(b),
ii) $(C_3-C_7)$-cycloalkyl,
iii) Cl, Br, I, F, and
iv) $CF_3$, or
(b) $(C_1-C_4)$-perfluoroalkyl; and
x is: a carbon-carbon single bond.

* * * * *